United States Patent
Kleinen et al.

(10) Patent No.: US 9,320,697 B2
(45) Date of Patent: Apr. 26, 2016

(54) SURFACTANT COMPOSITIONS AND FORMULATIONS WITH A HIGH OIL CONTENT

(71) Applicant: Evonik Industries AG, Essen (DE)

(72) Inventors: Jochen Kleinen, Heinsberg (DE); Uta Kortemeier, Essen (DE); Christian Hartung, Essen (DE); Joachim Venzmer, Essen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/684,887

(22) Filed: Apr. 13, 2015

(65) Prior Publication Data

US 2015/0297489 A1    Oct. 22, 2015

(30) Foreign Application Priority Data

Apr. 17, 2014 (DE) .......................... 10 2014 207 386

(51) Int. Cl.

| | | |
|---|---|---|
| *A61K 8/46* | (2006.01) | |
| *A61K 8/42* | (2006.01) | |
| *A61Q 19/00* | (2006.01) | |
| *A61K 8/44* | (2006.01) | |
| *C11D 1/94* | (2006.01) | |
| *C11D 17/00* | (2006.01) | |
| *A61Q 19/10* | (2006.01) | |
| *A61K 8/06* | (2006.01) | |
| *A61K 8/92* | (2006.01) | |
| *C11D 1/12* | (2006.01) | |
| *C11D 1/88* | (2006.01) | |
| *C11D 1/90* | (2006.01) | |

(52) U.S. Cl.
CPC . *A61K 8/46* (2013.01); *A61K 8/062* (2013.01); *A61K 8/42* (2013.01); *A61K 8/44* (2013.01); *A61K 8/463* (2013.01); *A61K 8/466* (2013.01); *A61K 8/92* (2013.01); *A61K 8/922* (2013.01); *A61Q 19/00* (2013.01); *A61Q 19/10* (2013.01); *C11D 1/94* (2013.01); *C11D 17/0026* (2013.01); *A61K 2800/48* (2013.01); *A61K 2800/596* (2013.01); *C11D 1/123* (2013.01); *C11D 1/88* (2013.01); *C11D 1/90* (2013.01)

(58) Field of Classification Search
None
See application file for complete search history.

(56) References Cited

U.S. PATENT DOCUMENTS

| | | |
|---|---|---|
| 3,650,964 A | 3/1972 | Sedliar et al. |
| 4,243,549 A | 1/1981 | Messenger et al. |
| 8,993,792 B2 | 3/2015 | Hartung et al. |
| 2002/0169093 A1 | 11/2002 | Muller et al. |
| 2003/0008792 A1 | 1/2003 | Shaukat et al. |
| 2003/0153631 A1 | 8/2003 | Slone et al. |
| 2005/0227892 A1 | 10/2005 | Shaukat et al. |
| 2012/0066839 A1 | 3/2012 | Man et al. |

FOREIGN PATENT DOCUMENTS

| | | | |
|---|---|---|---|
| EP | 0232153 A2 | 8/1987 | |
| WO | WO 2008/118381 A1 * | 10/2008 | ............... A61K 8/04 |

* cited by examiner

*Primary Examiner* — Brian J Davis
(74) *Attorney, Agent, or Firm* — Scully, Scott, Murphy & Presser, P.C.

(57) ABSTRACT

The invention relates to compositions which can be used for preparing structured formulations, to structured formulations comprising these compositions, and to processes for the preparation of structured formulations.

14 Claims, 1 Drawing Sheet

SURFACTANT COMPOSITIONS AND FORMULATIONS WITH A HIGH OIL CONTENT

FIELD OF THE INVENTION

The present invention relates to compositions which can be used for preparing structured formulations, to structured formulations comprising these compositions, and to processes for preparing structured formulations.

PRIOR ART

Structured surfactant-containing formulations are liquid crystalline compositions in which the surfactants are present in the form of planar and/or spherolithic lamellar phases. Usually, the surfactant phases are present in dispersed form as spheroliths, i.e., as lamellar droplets in the aqueous phase. Such spheroliths consist of an onion-like configuration of concentric double layers of surfactant molecules between which water or electrolyte solution is trapped. Structured surfactant compositions are typically pumpable, non-Newton compositions which are able to suspend water-insoluble particles, such as, for example oil droplets, on account of the presence of these lamellar surfactant phases.

Such structured formulations are used, for example, in cosmetic cleansing formulations such as shampoo, shower gel, soap, face cleanser, foam bath and body care formulations such as lotions, creams, conditioners, shaving products and baby care formulations.

An excellent property of such structured formulations is their ability to efficiently deposition substances present therein on a surface upon the addition of water.

WO 2008118381 discloses structured surface-active compositions comprising, based on 100 parts by weight of the composition, (I) from more than 0 to about 15 parts by weight of an alkyl ether sulfate surfactant,
(II) more than 0 to about 15 parts by weight of an alkyl sulfate surfactant,
(III) more than 0 to about 8 parts by weight of an alkanolamide surfactant,
(IV) 0 to about 10 parts by weight of an amphoteric surfactant, with the proviso that the total amount of components (I), (II), (III) and (IV) is greater than or equal to 5 parts by weight,
(V) an amount of an electrolyte which, in combination with the components (I), (II), (III) and (IV), causes a structured surfactant composition with an opaque visual appearance and a yield point of more than 0 Pascals to be produced, and (VI) water.

A disadvantage of the formulations described in the prior art is that such formulations do not have a particularly good foaming behaviour.

The necessary content of alkyl ether sulfates in the formulations of the prior art is likewise disadvantageous.

A further disadvantage of the structured formulations of the prior art is that the ratio of surfactants to contained oils is high.

In view of the above, there is a need to provide readily foaming, structured formulations with a high oil fraction, such as, for example, 20-60% by weight, based on the total formulation.

SUMMARY OF THE INVENTION

Surprisingly, Applicant has found that with the help of the composition comprising at least one substance selected from dialkyl sulfosuccinates and dialkylethylsulfosuccinates, at least one amphoteric surfactant and least one anionic surfactant it is possible to prepare readily foaming, structured formulations with a high oil fraction. The present invention is very surprising since dialkyl sulfosuccinates as described, for example, in U.S. Pat. No. 3,650,964 are generally known as poorly foaming surfactants, and that formulations with a high oil content, which comprise, for example, more than 10% by weight of oil, normally exhibit only low foam in cosmetic applications.

The present invention therefore provides compositions comprising:

A) 20 parts by weight to 67 parts by weight, of at least one substance selected from dialkyl sulfosuccinates and dialkyl methylsulfosuccinates,
B) 15 parts by weight to 40 parts by weight, of at least one amphoteric surfactant, and
C) 15 parts by weight to 40 parts by weight, of at least one anionic surfactant.

The present invention further provides structured formulations comprising the compositions according to the invention.

The present invention yet further provides processes for preparing the structured formulations according to the invention.

One advantage of the present invention is that large amounts of oil can be incorporated into the formulations according to the invention.

It is a further advantage of the present invention that the formulations according to the invention can be made sulfate-free, in particular ether-sulfate-free.

A further advantage of the present invention is that the formulations according to the invention can be made polyether-free.

A yet further advantage of the present invention is that the formulations according to the invention can stably comprise a very large amount of oil, based on the amount of surfactant present.

It is a further advantage that the formulations can be formulated very mild with regard to skin and eye irritation potential.

It is a further advantage of the present invention that the formulations according to the invention are storage-stable, both at elevated and reduced temperatures, as well as up on temperature fluctuations.

A further advantage of the present invention is that the formulations according to the invention can stably comprise fragrances, active ingredients and care substances and are able to deposition these to a high degree. This has the advantage that, e.g., the fragrance is spread evenly on the surface and is released over a prolonged period.

It is a further advantage of the present invention that the formulations according to the invention can be prepared in part cold and/or without the input of a large amount of energy.

A yet further advantage of the present invention is that the formulations according to the invention can be formulated without fatty acids and fatty alcohols.

A further advantage of the present invention is that the formulations according to the invention can have a yield point without the addition of polymeric rheological additives.

A further advantage of the present invention is that the formulations according to the invention are high-foaming despite the high fraction of oil.

A further advantage of the present invention is that the formulations according to the invention can be readily rinsed off.

A yet further advantage of the present invention is that the skin feel is improved during and after washing.

A further advantage of the present invention is the improved resistance to washing of oxidative hair colours.

A further advantage of the present invention is that the formulations according to the invention lead, upon application to the hair, to improved shine and to improved conditioning of the hair.

A yet further advantage of the present invention is the special creamy and rich texture of the formulations which can be obtained. Moreover, this texture can be attained without adding relatively large amounts of salt.

BRIEF DESCRIPTION OF THE DRAWINGS

The sole drawing of the present invention, i.e.

DETAILED DESCRIPTION OF THE INVENTION

As stated above, the composition according to the invention comprises:
A) 20 parts by weight to 67 parts by weight, preferably 25 parts by weight to 57 parts by weight, particularly preferably 33 parts by weight to 47 parts by weight, of at least one substance selected from dialkyl sulfosuccinates and dialkyl methylsulfosuccinates,
B) 15 parts by weight to 40 parts by weight, preferably 20 parts by weight to 32 parts by weight, particularly preferably 23 parts by weight to 28 parts by weight, of at least one amphoteric surfactant, and
C) 15 parts by weight to 40 parts by weight, preferably 20 parts by weight to 32 parts by weight, particularly preferably 23 parts by weight to 28 parts by weight, of at least one anionic surfactant.

In connection with the present invention, the term "surfactant" is understood as meaning organic substances with interface-active properties which have the ability to reduce the surface tension of water at 20° C. and at a concentration of 0.5% by weight, based on the total composition, to less than 45 mN/m. The surface tension is determined in the present invention by a ring method in accordance with DuNoüy at 25° C.

In connection with the present invention, the term "alkyl" includes alkyl radicals which may optionally be unsaturated.

In connection with the present invention, the term "amphoteric surfactant" is understood as meaning a zwitterionic surfactant in which, at a pH of 7 and 20° C., at least 90 mol % of the molecules have both in each case at least one negatively and positively charged group. Preferably, the amphoteric surfactants have an isoelectric point of $pH_{IEP}$=2-12 at 25° C.; the measurement being made in an aqueous 10 millimolar potassium chloride solution as a background electrolyte.

In connection with the present invention, the term "anionic surfactant" is understood as meaning a surfactant in which, at a pH of 7 and 20° C., at least 90 mol % of the molecules have at least one negatively charged group. Preferably, the anionic surfactants have no isoelectric point of $pH_{IEP}$=2-12 at 25° C.; the measurement being made in an aqueous 10 millimolar potassium chloride solution as a background electrolyte. Dialkyl sulfosuccinates and dialkyl methylsulfosuccinates are excluded here.

Unless stated otherwise, all of the stated percentages (%) are percent by mass. If, in preferred embodiments of the present invention, one or more of the contained components are limited to at least one defined substance, then this is to be understood as meaning that no further substance of the component apart from those specified is present in the composition or in the formulation.

Preferably, dialkyl sulfosuccinates and/or dialkyl methylsulfosuccinates present in the composition according to the invention are selected from the group consisting of dialkyl sulfosuccinates and/or dialkyl methylsulfosuccinates, in which the alkyl radicals have 4 to 24, preferably 6 to 18, particularly preferably 6 to 14, carbon atoms. The alkyl radicals can be linear or branched, with branched being preferred. Different or identical alkyl radicals can be present in one molecule of dialkyl sulfosuccinate and/or dialkyl methylsulfosuccinate, with identical being preferred.

As a counterion to the sulfonic acid group, preferably alkali metal cations, alkaline earth metal cations or ammonium ions, in particular sodium, can be used.

Particularly preferably present dialkyl sulfosuccinates are selected from the group consisting of Diethylhexyl Sodium Sulfosuccinate, Dinonyl Sodium Sulfosuccinate, Diisononyl Sodium Sulfosuccinate, Dioctyl Sodium Sulfosuccinate, Diheptyl Sodium Sulfosuccinate, Dihexyl Sodium Sulfosuccinate, Dineopentyl Sodium Sulfosuccinate, Diisoamyl Sodium Sulfosuccinate, Dipentyl Sodium Sulfosuccinate, Diamyl Sodium Sulfosuccinate, Dibutyl Sodium Sulfosuccinate, Diisobutyl Sodium Sulfosuccinate, Dicapryl Sodium Sulfosuccinate, Didecyl Sodium Sulfosuccinate, Diundecyl Sodium Sulfosuccinate, Dilauryl Sodium Sulfosuccinate, Dicocoyl Sodium Sulfosuccinate, Ditridecyl Sodium Sulfosuccinate, Dipropylheptyl Sodium Sulfosuccinate, Dicyclohexyl Sodium Sulfosuccinate, Ammonium Diethylhexyl Sulfosuccinate, Ammonium Dinonyl Sulfosuccinate, Ammonium Diisononyl Sulfosuccinate, Ammonium Dioctyl Sodium Sulfosuccinate, Ammonium Diheptyl Sulfosuccinate, Ammonium Dihexyl Sulfosuccinate, Ammonium Dineopentyl Sulfosuccinate, Ammonium Diisoamyl Sulfosuccinate, Ammonium Dipentyl Sulfosuccinate, Ammonium Diamyl Sulfosuccinate, Ammonium Dibutyl Sulfosuccinate, Ammonium Diisobutyl Sulfosuccinate, Ammonium Dicapryl Sulfosuccinate, Ammonium Didecyl Sulfosuccinate, Ammonium Diundecyl Sulfosuccinate, Ammonium Dilauryl Sulfosuccinate, Ammonium Dicocoyl Sulfosuccinate, Ammonium Ditridecyl Sulfosuccinate, Ammonium Dipropylheptyl Sulfosuccinate, Ammonium Dicyclohexyl Sulfosuccinate, Diethylhexyl Potassium Sulfosuccinate, Dinonyl Potassium Sulfosuccinate, Diisononyl Potassium Sulfosuccinate, Dioctyl Potassium Sulfosuccinate, Diheptyl Potassium Sulfosuccinate, Dihexyl Potassium Sulfosuccinate, Dineopentyl Potassium Sulfosuccinate, Diisoamyl Potassium Sulfosuccinate, Dipentyl Potassium Sulfosuccinate, Diamyl Potassium Sulfosuccinate, Dibutyl Potassium Sulfosuccinate, Diisobutyl Potassium Sulfosuccinate, Dicapryl Potassium Sulfosuccinate, Didecyl Potassium Sulfosuccinate, Diundecyl Potassium Sulfosuccinate, Dilauryl Potassium Sulfosuccinate, Dicocoyl Potassium Sulfosuccinate, Ditridecyl Potassium Sulfosuccinate, Dipropylheptyl Potassium Sulfosuccinate, Dicyclohexyl Potassium Sulfosuccinate, Diethylhexyl Sodium Methylsulfosuccinate, Dinonyl Sodium Methylsulfosuccinate, Diisononyl Sodium Methylsulfosuccinate, Dioctyl Sodium Methylsulfosuccinate, Diheptyl Sodium Methylsulfosuccinate, Dihexyl Sodium Methylsulfosuccinate, Dineopentyl Sodium Methylsulfosuccinate, Diisoamyl Sodium Methylsulfosuccinate, Dipentyl Sodium Methylsulfosuccinate, Diamyl Sodium Methylsulfosuccinate, Dibutyl Sodium Methylsulfosuccinate, Diisobutyl Sodium Methylsulfosuccinate, Dicapryl Sodium Methylsulfosuccinate, Didecyl Sodium Methylsulfosuccinate, Diundecyl Sodium Methylsulfosuccinate, Dilauryl Sodium Methylsulfosuccinate, Dicocoyl Sodium Methylsulfosuccinate, Ditridecyl Sodium Methylsulfosuccinate, Dipropylheptyl Sodium Methylsulfosuccinate, and Dicyclohexyl Sodium Methylsulfosuccinate, with Diethylhexyl Sodium Sulfosuccinate being very particularly preferred.

Preferably, amphoteric surfactants present in the composition according to the invention are selected from the group comprising, preferably consisting of, alkylbetaines, alkylamidoalkylbetaines, alkyl amphoacetates, alkyl amphodiacetates, alkyl amphopropionates, alkyl amphodipropionates, alkylsultaines, alkylhydroxysultaines, alkylamine oxides, alkyl amphoglycinates, alkyl iminodiacetates, alkyl iminodipropionates, alkylamphopropylsulfonates, alkyl amphocarboxyglycinates and alkyl amphocarboxypropionates.

Particularly preferably, amphoteric surfactants present in the composition according to the invention are selected from the group comprising, preferably consisting of, C4- to C24-, preferably C6- to C18-, particularly preferably C8- to C14-, alkylbetaines and C4- to C24-, preferably C6- to C18-, particularly preferably C8- to C14-, alkylamidopropylbetaines. The alkyl radicals can be linear or branched, with linear being preferred. Particularly preferably present alkylbetaines or alkylamidopropylbetaines are selected from the group consisting of Lauryl Betaine, Coco-Betaine, Behenyl Betaine, Capryl/Capramidopropyl Betaine, Cetyl Betaine, Cocamidoethyl Betaine, Cocamidopropyl Betaine, Coco/Oleamidopropyl Betaine, Decyl Betaine, Dimer Dilinoleamidopropyl Dibetaine, Hydrogenated Tallow Betaine, Hydroxylauryl/ Hydroxymyristyl Betaine, Isostearamidopropyl Betaine, Lauramidopropyl Betaine, Lauryl Betaine, Myristyl Betaine, Oleamidopropyl Betaine, Oleyl Betaine, Palmitamidopropyl Betaine, Ricinoleamidopropyl Betaine, Stearamidopropyl Betaine, Stearyl Betaine, Tallowamidopropyl Betaine, Tallow Betaine, Tallow Dihydroxyethyl Betaine, Undecylenamidopropyl Betaine, Sunfloweramidopropyl Betaine, Cetyl Betaine, and Lauryl Betaine.

Particularly preferably, alkyl amphoacetates, alkyl amphodiacetates, alkyl amphopropionates or alkyl amphodipropionates present according to the invention as amphoteric surfactants are selected from the group consisting of Cocobetainamido Amphopropionate, DEA-Cocoamphodipropionate, Disodium Caproamphodiacetate, Disodium Caproamphodipropionate, Disodium Caprylamphodiacetate, Disodium Caprylamphodipropionate, Disodium Cocoamphodiacetate, Disodium Cocoamphodipropionate, Disodium Isostearoamphodiacetate, Disodium Isostearoamphodipropionate, Disodium Laureth-5 Carboxyamphodiacetate, Disodium Lauroamphodiacetate, Disodium Lauroamphodipropionate, Disodium Oleoamphodipropionate, Disodium PPG-2-Isodeceth-7 Carboxyamphodiacetate, Disodium Stearoamphodiacetate, Disodium Tallowamphodiacetate, Sodium Caproamphopropionate, Sodium Caprylamphoacetate, Sodium Caprylamphopropionate, Sodium Cocoamphoacetate, Sodium Cocoamphopropionate, Sodium Isostearoamphoacetate, Sodium Isostearoamphopropionate, Sodium Lauroamphoacetate, Sodium Lauroamphopropionate, Sodium Myristoamphoacetate, Sodium Oleoamphoacetate, Sodium Oleoamphopropionate, Sodium Stearoamphoacetate, Sodium Stearoamphopropionate, Sodium Tallamphopropionate, Sodium Tallowamphoacetate, Sodium Undecylenoamphoacetate and Sodium Undecylenoamphopropionate.

Particularly preferably, alkylsultaines or alkylhydroxysultaines present according to the invention as amphoteric surfactants are selected from the group consisting of Capryl Sultaine, Cocamidopropyl Hydroxysultaine, Coco-Hydroxysultaine, Coco-Sultaine, Erucamidopropyl Hydroxysultaine, Lauramidopropyl Hydroxysultaine, Lauryl Hydroxysultaine, Lauryl Sultaine, Myristamidopropyl Hydroxysultaine, Oleamidopropyl Hydroxysultaine, and Tallowamidopropyl Hydroxysultaine.

Particularly preferably, alkylamine oxides present as amphoteric surfactants are selected from the group consisting of Behenamine Oxide, Cocamidopropylamine Oxide, Cocamine Oxide, Decylamine Oxide, Decyltetradecylamine Oxide, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Hydrogenated Tallowamine Oxide, Isostearamidopropylamine Oxide, Lauramidopropylamine Oxide, Lauramine Oxide, Myristamidopropylamine Oxide, Myristamine Oxide, Palmitamidopropylamine Oxide, Palmitamine Oxide, PEG-3 Lauramine Oxide, Stearamidopropylamine Oxide, Stearamine Oxide, Tallowamidopropylamine Oxide, Tallowamine Oxide, and Undecylenamidopropylamine Oxide.

Particularly preferably, alkyl amphoglycinates present as amphoteric surfactants are selected from the group consisting of Caproamphoglycinate, Capryloamphoglycinate, Cocoamphoglycinate, Iso stearoamphoglycinate, Lauroamphoglycinate, Myristoamphoglycinate, Oleoamphoglycinate, Stearoamphoglycinate, Tallowamphoglycinate, and Undecylenoamphoglycinate.

Particularly preferably, alkyl iminodiacetates or alkyl iminodipropionates present as amphoteric surfactants are selected from the group consisting of Disodium Cocaminopropyl Iminodiacetate, Disodium Hydroxyethyliminodiacetate, Disodium Lauriminodiacetate, Disodium Lauriminodipropionate, Disodium Steariminodipropionate, Disodium Tallowiminodipropionate, Sodium C12-15 Alkoxypropyl Iminodipropionate, Sodium Cocoiminodiacetate, and Sodium Lauriminodipropionate.

Particularly preferably, alkylamphopropylsulfonates present as amphoteric surfactants are selected from the group consisting of Sodium Cocoamphohydroxypropylsulfonate, Sodium Lauroamphohydroxypropylsulfonate, Sodium Oleoamphohydroxypropylsulfonate, Sodium Stearoamphohydroxypropylsulfonate, Disodium Lauriminobishydroxypropylsulfonate, Disodium Cocoamphocarboxyethylhydroxypropylsulfonate, Sodium Caproamphohydroxypropylsulfonate, and Sodium Caprylamphohydroxypropylsulfonate.

Very particularly preferably, the amphoteric surfactant present is Cocamidopropyl Betaine.

Preferably, anionic surfactants present in the composition according to the invention are selected from the group comprising, preferably consisting of, alkyl sulfates, alkyl ether sulfates, optionally alkoxylated sulfosuccinates, optionally alkoxylated methylsulfosuccinates, optionally alkoxylated sulfonates, optionally alkoxylated glycinates, optionally alkoxylated glutamates, optionally alkoxylated isethionates, optionally alkoxylated carboxylates, optionally alkoxylated anisates, optionally alkoxylated levulinates, optionally alkoxylated tartrates, optionally alkoxylated lactylates, optionally alkoxylated taurates, optionally alkoxylated alaninates, optionally alkoxylated phosphates, optionally alkoxylated sulfoacetates, optionally alkoxylated sulfosuccinamates, optionally alkoxylated sarcosinates and optionally alkoxylated phosphonates. In this context, dialkyl sulfosuccinates are excluded from the sulfosuccinates and dialkyl methylsulfosuccinates are excluded from the methylsulfosuccinates.

Preferably, alkyl sulfates or alkyl ether sulfates present as anionic surfactant in the composition according to the invention are selected from the group consisting of C4- to C24-, preferably C6- to C18-, particularly preferably C8- to C14-, alkyl sulfates and alkyl ether sulfates. The alkyl radicals can be linear or branched, with linear being preferred. Suitable branched alkyl radicals include methyldecyl groups, methylundecyl groups, methyldodecyl groups, ethyldecyl groups, ethylundecyl groups and ethyldodecyl groups, such as for example 1-methyldecyl, 1-methylundecyl, 1-methyldodecyl, 1-ethyldecyl, 1-ethylundecyl and 1-ethyldodecyl.

The addition of an alkyl or alkenyl group with the suffix "eth" describes in general the addition of one or more ethylene oxide units, for example trideceth refers to an ethoxylated tridecyl group, and the suffix "-n", where n is an integer, the number of such ethylene oxide units per group, for example "Trideceth-3" refers to a group of ethoxylated tridecyl alcohol with 3 ethylene oxide units per tridecyl group.

In a preferred embodiment, the alkyl sulfate or alkyl ether sulfate is selected from Ammonium C12-15 Alkyl Sulfate, Ammonium C12-16 Alkyl Sulfate, Ammonium Capryleth Sulfate, Ammonium Cocomonoglyceride Sulfate, Ammonium Coco-Sulfate, Ammonium C12-15 Pareth Sulfate, Ammonium Laureth Sulfate, Ammonium Laureth-5 Sulfate, Ammonium Laureth-7 Sulfate, Ammonium Laureth-9 Sulfate, Ammonium Laureth-12 Sulfate, Ammonium Lauryl Sulfate, Ammonium Myreth Sulfate, Ammonium Myristyl Sulfate, Ammonium Nonoxynol-4 Sulfate, Ammonium Nonoxynol-30 Sulfate, Ammonium Palm Kernel Sulfate, Ammonium Trideceth Sulfate, DEA-C12-13 Alkyl Sulfate, DEA-C12-15 Alkyl Sulfate, DEA-Cetyl Sulfate, DEA-C12-13 Pareth-3 Sulfate, DEA-Laureth Sulfate, DEA-Lauryl Sulfate, DEA-Myreth Sulfate, DEA-Myristyl Sulfate, DEA-Trideceth Sulfate, Diethylamine Laureth Sulfate, Magnesium Coceth Sulfate, Magnesium Coco-Sulfate, Magnesium Laureth Sulfate, Magnesium Laureth-5 Sulfate, Magnesium Laureth-8 Sulfate, Magnesium Laureth-16 Sulfate, Magnesium Lauryl Sulfate, Magnesium Myreth Sulfate, Magnesium Oleth Sulfate, Magnesium PEG-3 Cocamide Sulfate, Magnesium/TEA-Coco-Sulfate, MEA-Laureth Sulfate, MEA-Lauryl Sulfate, MEA-Trideceth Sulfate, MIPA C12-15 Pareth Sulfate, MIPA-Laureth Sulfate, MIPA-Lauryl Sulfate, MIPA-Trideceth Sulfate, Mixed Isopropanolamines Lauryl Sulfate, Potassium Laureth Sulfate, Potassium Lauryl Sulfate, Sodium C8-10 Alkyl Sulfate, Sodium C10-16 Alkyl Sulfate, Sodium C11-15 Alkyl Sulfate, Sodium C12-13 Alkyl Sulfate, Sodium C12-15 Alkyl Sulfate, Sodium C12-18 Alkyl Sulfate, Sodium C16-20 Alkyl Sulfate, Sodium Caprylyl Sulfate, Sodium Cetearyl Sulfate, Sodium Cetyl Sulfate, Sodium Cholesteryl Sulfate, Sodium Coceth Sulfate, Sodium Coceth-30 Sulfate, Sodium Coco/Hydrogenated Tallow Sulfate, Sodium Cocomonoglyceride Sulfate, Sodium Coco-Sulfate, Sodium C9-15 Pareth-3 Sulfate, Sodium C10-15 Pareth Sulfate, Sodium C10-16 Pareth-2 Sulfate, Sodium C12-13 Pareth Sulfate, Sodium C12-14 Pareth-3 Sulfate, Sodium C12-15 Pareth Sulfate, Sodium C12-15 Pareth-3 Sulfate, Sodium C13-15 Pareth-3 Sulfate, Sodium C12-14 Sec-Pareth-3 Sulfate, Sodium Deceth Sulfate, Sodium Decyl Sulfate, Sodium Ethylhexyl Sulfate, Sodium Laneth Sulfate, Sodium Laureth Sulfate, Sodium Laureth-5 Sulfate, Sodium Laureth-7 Sulfate, Sodium Laureth-8 Sulfate, Sodium Laureth-12 Sulfate, Sodium Laureth-40 Sulfate, Sodium Lauryl Sulfate, Sodium/MEA-PEG-3 Cocamide Sulfate, Sodium Myreth Sulfate, Sodium Myristyl Sulfate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8 Sulfate, Sodium Nonoxynol-10 Sulfate, Sodium Nonoxynol-25 Sulfate, Sodium Octoxynol-2 Sulfate, Sodium Octoxynol-6 Sulfate, Sodium Octoxynol-9 Sulfate, Sodium Oleth Sulfate, Sodium Oleyl Sulfate, Sodium PEG-4 Cocamide Sulfate, Sodium PEG-4 Lauramide Sulfate, Sodium Stearyl Sulfate, Sodium Tallow Sulfate, Sodium/TEA C12-13 Pareth-3 Sulfate, Sodium Trideceth Sulfate, Sodium Tridecyl Sulfate, Sulfated Castor Oil, Sulfated Coconut Oil, Sulfated Glyceryl Oleate, Sulfated Olive Oil, Sulfated Peanut Oil, TEA-C10-15 Alkyl Sulfate, TEA-C11-15 Alkyl Sulfate, TEA-C12-13 Alkyl Sulfate, TEA-C12-14 Alkyl Sulfate, TEA-C12-15 Alkyl Sulfate, TEA-Coco-Sulfate, TEA-C11-15 Pareth Sulfate, TEA-C12-13 Pareth-3 Sulfate, TEA-Laneth-5 Sulfate, TEA-Laureth Sulfate, TEA-Lauryl Sulfate, TEA-Oleyl Sulfate, TEA-PEG-3 Cocamide Sulfate, TEA-Trideceth Sulfate, TIPA-Laureth Sulfate, and TIPA-Lauryl Sulfate, with Sodium Laureth Sulfate being very particularly preferred.

Preferably, optionally alkoxylated sulfosuccinates and/or methylsulfosuccinates present as anionic surfactant in the composition according to the invention are selected from the group consisting of optionally alkoxylated C4- to C24-, preferably C6- to C18-, particularly preferably C8- to C14-, sulfosuccinates and/or methylsulfosuccinates. The alkyl radicals can be linear or branched, with linear being preferred. Alkoxylated sulfosuccinates and/or methylsulfosuccinates can in particular have a degree of alkoxylation between 1 and 10, particularly preferably between 2 and 5.

The alkoxy group is preferably selected from ethoxy.

Particularly preferably, optionally alkoxylated sulfosuccinates present are selected from the group consisting of Disodium Laureth Sulfosuccinate, Disodium C12-14 Pareth-1 Sulfosuccinate, Disodium C12-14 Pareth-2 Sulfosuccinate, Disodium C12-14 Sec-pareth-12 Sulfosuccinate, Disodium C12-14 Sec-pareth-3 Sulfosuccinate, Disodium C12-14 Sec-pareth-5 Sulfosuccinate, Disodium C12-14 Sec-pareth-7 Sulfosuccinate, Disodium C12-14 Sec-pareth-9 Sulfosuccinate, Disodium C12-14 Pareth Sulfosuccinate, Di-Triethanolamine Oleamido PEG-2 Sulfosuccinate, Disodium Oleamido PEG-2 Sulfosuccinate, Disodium Cocamido Monoisopropanolamine PEG-4 Sulfosuccinate, Disodium Cocamido PEG-4 Sulfosuccinate, Disodium Coceth-3 Sulfosuccinate, Disodium Cocoyl Butyl Gluceth-10 Sulfosuccinate, Disodium Deceth-5 Sulfosuccinate, Disodium Deceth-6 Sulfosuccinate, Disodium Laneth-5 Sulfosuccinate, Disodium Lauramido PEG-2 Sulfosuccinate, Disodium Lauramido PEG-5 Sulfosuccinate, Disodium Laureth Sulfosuccinate, Disodium Laureth-12 Sulfosuccinate, Disodium Laureth-6 Sulfosuccinate, Disodium Laureth-9 Sulfosuccinate, Disodium Oleamido PEG-2 Sulfosuccinate, Disodium Oleth-3 Sulfosuccinate, Disodium Palmitamido PEG-2 Sulfosuccinate, Disodium PEG-5 Laurylcitrate Sulfosuccinate, Disodium PEG-8 Palm Glycerides Sulfosuccinate, Disodium Sitostereth-14 Sulfosuccinate, Disodium Undecylenamide PEG-2 Sulfosuccinate, Magnesium Laureth-3 Sulfosuccinate, Monoethanolamine Laureth-2 sulfosuccinate, Diammonium C12-14 Pareth-1 Sulfosuccinate, Diammonium C12-14 Pareth-2 Sulfosuccinate, Diammonium C12-14 Sec-pareth-12 Sulfosuccinate, Diammonium C12-14 Sec-pareth-3 Sulfosuccinate, Diammonium C12-14 Sec-pareth-5 Sulfosuccinate, Diammonium C12-14 Sec-pareth-7 Sulfosuccinate, Diammonium C12-14 Sec-pareth-9 Sulfosuccinate, Diammonium C12-14 Pareth Sulfosuccinate, Di-Triethanolamine Oleamido PEG-2 Sulfosuccinate, Diammonium Oleamido PEG-2 Sulfosuccinate, Diammonium Cocamido Monoisopropanolamine PEG-4 Sulfosuccinate, Diammonium Cocamido PEG-4 Sulfosuccinate, Diammonium Coceth-3 Sulfosuccinate, Diammonium Cocoyl Butyl Gluceth-10 Sulfosuccinate, Diammonium Deceth-5 Sulfosuccinate, Diammonium Deceth-6 Sulfosuccinate, Diammonium Laneth-5 Sulfosuccinate, Diammonium Lauramido PEG-2 Sulfosuccinate, Diammonium Lauramido PEG-5 Sulfosuccinate, Diammonium Laureth Sulfosuccinate, Diammonium Laureth-12 Sulfosuccinate, Diammonium Laureth-6 Sulfosuccinate, Diammonium Laureth-9 Sulfosuccinate, Diammonium Oleamido PEG-2 Sulfosuccinate, Diammonium Oleth-3 Sulfosuccinate, Diammonium Palmitamido PEG-2 Sulfosuccinate, Diammonium PEG-5 Laurylcitrate Sulfosuccinate, Disodium PEG-8 Palm Glycerides Sulfosuccinate, Diammonium Sitostereth-14 Sulfosuccinate, Diammonium Undecylenamide PEG-2 Sulfosuccinate, Ammonium Lauryl Sulfosuccinate, Diammonium Lauramido-MEA Sulfosuccinate, Diammonium Lauryl Sulfosuccinate, Dipotassium Lauryl Sulfosuccinate, Disodium Babassuamido MEA-Sulfosuccinate, Disodium Cetearyl Sulfosuccinate, Disodium Cetyl Sulfosuccinate, Disodium Cocamido MEA-Sulfosuccinate, Disodium Cocamido MIPA-Sulfosuccinate, Disodium Coco-Glucoside Sulfosuccinate, Disodium Coco-Sulfosuccinate, Disodium Hydrogenated Cottonseed Glyceride Sulfosuccinate, Disodium Isodecyl Sulfosuccinate, Disodium Isostearamido MEA-Sulfosuccinate, Disodium Isostearamido MIPA-Sulfosuccinate, Disodium Isostearyl Sulfosuccinate, Disodium Lauramido MEA-Sulfosuccinate, Disodium Lauramido MIPA Glycol Sulfosuccinate, Disodium Lauryl Sulfosuccinate, Disodium Myristamido MEA-Sulfosuccinate, Disodium Oleamido MEA-Sulfosuccinate, Disodium Oleamido MIPA-Sulfosuccinate, Disodium Oleyl Sulfosuccinate, Disodium Polyglyceryl-3 Caprate/Caprylate Sulfosuccinate, Disodium Ricinoleamido MEA-Sulfosuccinate, Disodium Stearamido MEA-Sulfosuccinate, Disodium Stearyl Sulfosuccinate, Disodium Tallamido MEA-Sulfosuccinate, Disodium Tallowamido MEA-Sulfosuccinate, Disodium Tridecylsulfosuccinate, and Disodium Undecylenamido MEA-Sulfosuccinate, with Disodium Laureth Sulfosuccinate being very particularly preferred.

Preferably, optionally alkoxylated sulfonates present as anionic surfactant in the composition according to the invention are selected from the group consisting of Sodium C14-16 Olefin Sulfonate, Sodium C12-15 Pareth-15 Sulfonate, Sodium C14-17 Alkyl sec. Sulfonate, Sodium C14 Olefin Sulfonate, Ammonium Cumenesulfonate, Ammonium Dodecylbenzenesulfonate, Calcium Dodecylbenzenesulfonate, DEA-Dodecylbenzenesulfonate, DEA-Methyl Myristate Sulfonate, Disodium Decyl Phenyl Ether Disulfonate, Disodium Lauriminobishydroxypropylsulfonate, Disodium Lauryl Phenyl Ether Disulfonate, Isopropylamine Dodecylbenzenesulfonate, Magnesium Isododecylbenzenesulfonate, Magnesium Lauryl Hydroxypropyl Sulfonate, MEA-C10-13 Alkyl Benzenesulfonate, MIPA-Dodecylbenzenesulfonate, Potassium Dodecylbenzenesulfonate, Potassium Lauryl Hydroxypropyl Sulfonate, Sodium C13-17 Alkane Sulfonate, Sodium C14-18 Alkane Sulfonate, Sodium C10-13 Alkyl Benzenesulfonate, Sodium C9-22 Alkyl Sec Sulfonate, Sodium C14-17 Alkyl Sec Sulfonate, Sodium Caproylethylformyl Benzenesulfonate, Sodium Caprylyl PG-Sulfonate, Sodium Caprylyl Sulfonate, Sodium Cocoglucosides Hydroxypropylsulfonate, Sodium Cocoglyceryl Ether Sulfonate, Sodium Cocomonoglyceride Sulfonate, Sodium C12-14 Olefin Sulfonate, Sodium C14-16 Olefin Sulfonate, Sodium C14-18 Olefin Sulfonate, Sodium C16-18 Olefin Sulfonate, Sodium C14-15 Pareth-PG Sulfonate, Sodium C12-15 Pareth-3 Sulfonate, Sodium C12-15 Pareth-7 Sulfonate, Sodium C12-15 Pareth-15 Sulfonate, Sodium Decylbenzenesulfonate, Sodium Decylglucosides Hydroxypropylsulfonate, Sodium Dodecylbenzenesulfonate, Sodium Hydroxypropyl Palm Kernelate Sulfonate, Sodium Lauryl Hydroxypropyl Sulfonate, Sodium Laurylglucosides Hydroxypropylsulfonate, Sodium Methyl Laurate Sulfonate, Sodium Methyl Myristate Sulfonate, Sodium Methyl Palmitate Sulfonate, Sodium Methyl Stearate Sulfonate, Sodium Palm Glyceride Sulfonate, Sodium Phenylnonanoate Sulfonate, Sodium Tridecylbenzenesulfonate, TEA C14-17 Alkyl Sec Sulfonate, TEA-Dodecylbenzenesulfonate, and TEA-Tridecylbenzenesulfonate.

Preferably, optionally alkoxylated glycinates present as anionic surfactant in the composition according to the invention are selected from the group consisting of Sodium Cocoyl Glycinate, Potassium Cocoyl Glycinate, Sodium Lauroyl Glycinate, Sodium Lauryl Diethylenediaminoglycinate, and TEA-Cocoyl Glycinate.

Preferably, optionally alkoxylated glutamates present as anionic surfactant in the composition according to the invention are selected from the group consisting of Sodium Cocoyl Glutamate, Disodium Cocoyl Glutamate, Sodium Lauroyl Glutamate, Sodium Cocoyl Hydrolyzed Wheat Protein Glutamate, Dipotassium Capryloyl Glutamate, Dipotassium Undecylenoyl Glutamate, Disodium Capryloyl Glutamate, Disodium Cocoyl Glutamate, Disodium Hydrogenated Tallow Glutamate, Disodium Lauroyl Glutamate, Disodium Stearoyl Glutamate, Disodium Undecylenoyl Glutamate, Potassium Capryloyl Glutamate, Potassium Cocoyl Glutamate, Potassium Lauroyl Glutamate, Potassium Myristoyl Glutamate, Potassium Stearoyl Glutamate, Potassium Undecylenoyl Glutamate, Sodium Capryloyl Glutamate, Sodium Cocoyl Glutamate, Sodium Cocoyl/Hydrogenated Tallow Glutamate, Sodium Cocoyl Hydrolyzed Wheat Protein Glutamate, Sodium Cocoyl/Palmoyl/Sunfloweroyl Glutamate, Sodium Hydrogenated Tallowoyl Glutamate, Sodium Lauroyl Glutamate, Sodium Myristoyl Glutamate, Sodium Olivoyl Glutamate, Sodium Palmoyl Glutamate, Sodium Stearoyl Glutamate, Sodium Undecylenoyl Glutamate, TEA-Cocoyl Glutamate, TEA-Hydrogenated Tallowoyl Glutamate, and TEA-Lauroyl Glutamate.

Preferably, optionally alkoxylated isethionates present as anionic surfactant in the composition according to the invention are selected from the group consisting of Sodium Lauroyl Methyl Isethionate, Sodium Cocoyl Isethionate, Ammonium Cocoyl Isethionate, Sodium Cocoyl Isethionate, Sodium Hydrogenated Cocoyl Methyl Isethionate, Sodium Lauroyl Isethionate, Sodium Lauroyl Methyl Isethionate, Sodium Myristoyl Isethionate, Sodium Oleoyl Isethionate, Sodium Oleyl Methyl Isethionate, Sodium Palm Kerneloyl Isethionate, and Sodium Stearoyl Methyl Isethionate.

Preferably, optionally alkoxylated carboxylates present as anionic surfactant in the composition according to the invention are selected from the group consisting of Trideceth-7 Carboxylic Acid, Sodium Laureth-13 Carboxylate, Sodium Laureth-4 Carboxylate, Laureth-11 Carboxylic Acid, Laureth-5 Carboxylic Acid, Sodium Laureth-5 Carboxylate, Ammonium Laureth-6 Carboxylate, Ammonium Laureth-8 Carboxylate, Capryleth-4 Carboxylic Acid, Capryleth-6 Carboxylic Acid, Capryleth-9 Carboxylic Acid, Ceteareth-25 Carboxylic Acid, Cetyl C12-15 Pareth-8 Carboxylate, Cetyl C12-15-Pareth-9 Carboxylate, Cetyl PPG-2 Isodeceth-7 Carboxylate, Coceth-7 Carboxylic Acid, C9-11 Pareth-6 Carboxylic Acid, C9-11 Pareth-8 Carboxylic Acid, C11-15 Pareth-7 Carboxylic Acid, C12-13 Pareth-5 Carboxylic Acid, C12-13 Pareth-7 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C12-15 Pareth-12 Carboxylic Acid, C14-15 Pareth-8 Carboxylic Acid, Deceth-7 Carboxylic Acid, Ethylhexeth-3 Carboxylic Acid, Hexeth-4 Carboxylic Acid, Isopropyl C12-15-

Pareth-9 Carboxylate, Isopropyl PPG-2 Isodeceth-7 Carboxylate, Isosteareth-6 Carboxylic Acid, Isosteareth-11 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Magnesium Laureth-11 Carboxylate, MEA-Laureth-6 Carboxylate, MEA PPG-6 Laureth-7 Carboxylate, MEA-PPG-8-Steareth-7 Carboxylate, Myreth-3 Carboxylic Acid, Myreth-5 Carboxylic Acid, Oleth-3 Carboxylic Acid, Oleth-6 Carboxylic Acid, Oleth-10 Carboxylic Acid, PEG-2 Stearamide Carboxylic Acid, PEG-9 Stearamide Carboxylic Acid, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Trideceth-3 Carboxylate, Potassium Trideceth-4 Carboxylate, Potassium Trideceth-7 Carboxylate, Potassium Trideceth-15 Carboxylate, Potassium Trideceth-19 Carboxylate, PPG-3-Deceth-2 Carboxylic Acid, Propyl C12-15 Pareth-8 Carboxylate, Sodium Capryleth-2 Carboxylate, Sodium Capryleth-9 Carboxylate, Sodium Ceteareth-13 Carboxylate, Sodium Ceteth-13 Carboxylate, Sodium C9-11 Pareth-6 Carboxylate, Sodium C11-15 Pareth-7 Carboxylate, Sodium C12-13 Pareth-5 Carboxylate, Sodium C12-13 Pareth-8 Carboxylate, Sodium C12-13 Pareth-12 Carboxylate, Sodium C12-15 Pareth-6 Carboxylate, Sodium C12-15 Pareth-7 Carboxylate, Sodium C12-15 Pareth-8 Carboxylate, Sodium C12-15 Pareth-12 Carboxylate, Sodium C14-15 Pareth-8 Carboxylate, Sodium C12-14 Sec-Pareth-8 Carboxylate, Sodium Deceth-2 Carboxylate, Sodium Hexeth-4 Carboxylate, Sodium Isosteareth-6 Carboxylate, Sodium Isosteareth-11 Carboxylate, Sodium Laureth-3 Carboxylate, Sodium Laureth-4 Carboxylate, Sodium Laureth-5 Carboxylate, Sodium Laureth-6 Carboxylate, Sodium Laureth-8 Carboxylate, Sodium Laureth-11 Carboxylate, Sodium Laureth-12 Carboxylate, Sodium Laureth-13 Carboxylate, Sodium Laureth-14 Carboxylate, Sodium Laureth-16 Carboxylate, Sodium Laureth-17 Carboxylate, Sodium Lauryl Glucose Carboxylate, Sodium Lauryl Glycol Carboxylate, Sodium PEG-6 Cocamide Carboxylate, Sodium PEG-8 Cocamide Carboxylate, Sodium PEG-3 Lauramide Carboxylate, Sodium PEG-4 Lauramide Carboxylate, Sodium PEG-7 Olive Oil Carboxylate, Sodium PEG-8 Palm Glycerides Carboxylate, Sodium Trideceth-3 Carboxylate, Sodium Trideceth-4 Carboxylate, Sodium Trideceth-6 Carboxylate, Sodium Trideceth-7 Carboxylate, Sodium Trideceth-8 Carboxylate, Sodium Trideceth-12 Carboxylate, Sodium Trideceth-15 Carboxylate, Sodium Trideceth-19 Carboxylate, Sodium Undeceth-5 Carboxylate, Trideceth-3 Carboxylic Acid, Trideceth-4 Carboxylic Acid, Trideceth-7 Carboxylic Acid, Trideceth-8 Carboxylic Acid, Trideceth-15 Carboxylic Acid, Trideceth-19 Carboxylic Acid and Undeceth-5 Carboxylic Acid.

Preferably, optionally alkoxylated sarcosinates present as anionic surfactant in the composition according to the invention are selected from the group consisting of Sodium Lauroyl Sarcosinate, Sodium Cocoyl Sarcosinate, Sodium Myristoyl Sarcosinate, TEA-Cocoyl Sarcosinate, Ammonium Cocoyl Sarcosinate, Ammonium Lauroyl Sarcosinate, Dimer Dilinoleyl Bis-Lauroylglutamate/Lauroylsarcosinate, Disodium Lauroamphodiacetate Lauroyl Sarcosinate, Isopropyl Lauroyl Sarcosinate, Potassium Cocoyl Sarcosinate, Potassium Lauroyl Sarcosinate, Sodium Cocoyl Sarcosinate, Sodium Lauroyl Sarcosinate, Sodium Myristoyl Sarcosinate, Sodium Oleoyl Sarcosinate, Sodium Palmitoyl Sarcosinate, TEA-Cocoyl Sarcosinate, TEA-Lauroyl Sarcosinate, TEA-Oleoyl Sarcosinate, and TEA-Palm Kernel Sarcosinate.

Further substances which may be present as anionic surfactant in the composition according to the invention are selected from the group consisting of Sodium Anisate, Sodium Levulinate, Sodium Coco-Glucoside Tartrate, Sodium Lauroyl Lactylate, Sodium Methyl Cocoyl Taurate, Sodium Methyl Lauroyl Taurate, Sodium Methyl Oleoyl Taurate, Sodium Cocoyl Alaninate, Sodium Laureth-4 Phosphate, Laureth-1 Phosphate, Laureth-3 Phosphate, Potassium Laureth-1 Phosphate, Sodium Lauryl Sulfoacetate and Sodium Coco Sulfoacetate, Disodium Stearyl Sulfosuccinamate, Disodium Tallow Sulfosuccinamate, Tetrasodium Dicarboxyethyl Stearyl Sulfosuccinamate, and their alkoxylated variants and mixtures thereof.

It is preferred according to the invention if the composition according to the invention additionally comprises a component D) 0 parts by weight to 15 parts by weight, preferably 5 parts by weight to 12 parts by weight, particularly preferably 7 parts by weight to 10 parts by weight, of at least one hydrophobic thickener.

Preferred hydrophobic thickeners which are preferably present in the formulation according to the invention are selected from the group comprising, preferably consisting of, reaction products of at least one fatty acid and/or at least one fatty acid ester, such as for example fatty acid glycerol esters, fatty acid methylesters and fatty acid ethylesters, with at least one primary or secondary amine, where the amine preferably additionally also comprises one or more other functional groups such as for example alcohols, and cationic surfactants in which, at a pH of 7 and 20° C., at least 90 mol % of the molecules have at least one positively charged group and preferably have no isoelectric point of $pH_{IEP}$=2-12 at 25° C.; the measurement being made in an aqueous 10 millimolar potassium chloride solution as a background electrolyte.

Preferably, hydrophobic thickeners present in the composition according to the invention are selected from the group comprising, preferably consisting of, alkamide monoethanolamines, alkamide dieethanolamines, alkamide monoisopropanolamines, ethoxylated fatty acid amides, fatty alcohol ethoxylates, alkyl quats and alkylamidoalkyl quats.

Preferably, alkamide monoethanolamines, alkamide dieethanolamines and alkamide monoisopropanolamines present as hydrophobic thickeners in the composition according to the invention are selected from the group comprising, preferably consisting of, C4- to C24-, preferably C6- to C18-, particularly preferably C8- to C14-, alkamide monoethanolamines, alkamide dieethanolamines and alkamide monoisopropanolamines. The alkyl radicals can be linear or branched, with linear being preferred. Particularly preferably, alkamide monoethanolamines, alkamide dieethanolamines and alkamide monoisopropanolamines present are selected from the group consisting of Cocamide Monoethanolamine (=Cocamide MEA), Minkamide Diethanolamine, Oliveamide Monoethanolamine, Palm Kernelamide Monoethanolamine, Palm Kernelamide Diethanolamine, Palm Kernelamide Monoisopropanolamine, Palmamide Monoethanolamine, Palmamide Diethanolamine, Palmamide Monoisopropanolamine, Peanutamide Monoethanolamine, Peanutamide Diethanolamine, Peanutamide Monoisopropanolamine, Soyamide Diethanolamine, Tallamide Diethanolamine, Tallowamide Diethanolamine, Tallowamide Monoethanolamine, Cocamide Diethanolamine (=Cocamide DEA), Cocamide Monoisopropanolamine (=Cocamide MIPA), Steramide Monoisopropanolamine, Isostearamide Monoisopropanolamine, Lauramide Monoisopropanolamine, Linoleamide Monoisopropanolamine, Myristamide Monoisopropanolamine, Oleamide Monoisopropanolamine, and Ricinoleamide Monoisopropanolamine, with Cocamide Monoethanolamine being very particularly preferred.

Compositions particularly preferred according to the invention comprise

A) 33 parts by weight to 47 parts by weight of Diethylhexyl Sodium Sulfosuccinate,
B) 23 parts by weight to 28 parts by weight of Cocamidopropyl Betaine,
C) 23 parts by weight to 28 parts by weight of at least one substance selected from Sodium Laureth Sulfate and Disodium Laureth Sulfosuccinate, and
D) 7 parts by weight to 10 parts by weight of Cocamide MEA.

In one aspect of the invention, the compositions according to the invention comprise, in addition to the components A) to D), a solvent such as, for example, water and/or propylene glycol, dipropylene glycol, ethanol, isopropanol, glycerol, in particular water, preferably in an amount of from 20% by weight to 85% by weight, preferably from 30% by weight to 70% by weight, particularly preferably from 40% by weight to 50% by weight, based on the total composition.

This has the technical effect that the compositions according to the invention can be fully formulated more easily, have better processability and are more storage-stable. In this aspect of the invention, it is preferred according to the invention if the sum of components A) to D) in the composition according to the invention is contained in an amount from 5% by weight to 80% by weight, preferably from 8% by weight to 70% by weight, particularly preferably from 10% by weight to 60% by weight, based on the total composition.

The compositions according to the invention are exceptionally suitable for the incorporation of large amounts of oil while retaining structured formulations, in particular structured cosmetic formulations.

Consequently, the present invention further provides a structured formulation, in particular a cosmetic formulation, comprising a composition according to the invention and E) at least one cosmetic oil in an amount of from 11% by weight to 74% by weight, preferably 16% by weight to 60% by weight, particularly preferably 21% by weight to 55% by weight, where the percentages by weight refer to the total formulation.

In connection with the present invention, the term "structured formulation" is to be understood as meaning a formulation which has a viscosity, which falls with increasing shear rate, in the shear rate range from 0.1 to 100 s$^{-1}$ and which has a yield point of >=1 mPa. Both the viscosity and the yield point is measured using a rheometer, the measurement axis of which is stored in an air bearing.

The viscosity drops in the stated shear rate range by 1-10 orders of magnitude, with 2-6 orders of magnitude being preferred. The measurements are carried out using a plate-plate geometry with a diameter of 40 mm at 25° C.

The yield point is measured in oscillation at a frequency of 1 Hz at 25° C. with a plate-plate geometry with a diameter of 40 mm. The shear stress is varied here from 0.001-100 Pa and the criterion taken for the yield point is the shear stress at which a deviation of 5% of the storage modulus from the plateau value of the linearly viscoelastic range is achieved.

Preferred structured formulations according to the invention have a yield point of more than 0.001 Pa and particularly preferably of 1-100 Pa. It is particularly preferred in this connection that the yield point of more than 0.001 Pa and preferably of 1-100 Pa is present in the absence of polymeric rheological additives in the formulation according to the invention.

Cosmetic oils that can be used are substances such as silicone oils, functionalized silicones, mineral oils, fatty acid esters, natural oils such as vegetable oils, animal oils, and mixtures thereof.

Preferred formulations according to the invention comprise Cyclopentasiloxane, Cyclomethicone, Dimethicone, Dimethiconol, Amodimethicone, PEG/PPG Dimethicones, Cetyl Dimethicone, Stearyl Dimethicone, Stearoxy Dimethicone, Behenoxy Dimethicone, Polyisobutene, Petrolatum, Mineral Oil, Hydrogenated Polydodecene, Hydrogenated Polydecene, Polydecene, Isoamyl Cocoate, PPG-3 Myristyl Ether, PPG-11 Stearyl Ether, Dicaprylyl Ether, Dicaprylyl Carbonate, Cetearyl Isononanoate, Cetyl Ethylhexanoate, Diethyhexyl Carbonate, Cetyl Ricinoleate, Myristyl Myristate, Stearyl Heptanoate, Decyl Cocoate, Decyl Oleate, PPG-15 Stearyl Ether, Octyldodecanol, Isocetyl Palmitate, Cetearyl Ethylhexanoate, Ethylhexyl Palmitate, Ethylhexyl Stearate, Isopropyl Palmitate, PPG-14 Butyl Ether, Triisostearin, C12-15 Alkyl Benzoate, Phenoxyethyl Caprylate, Isopropyl Myristate, Caprylic/Capric Triglyceride, sunflower oil, olive oil, argan oil, mineral oil, castor oil, ricinus oil, cocoa oil, palm oil, coconut oil, avocado oil, almond oil, jojoba oil, corn oil, rapeseed oil, sesame oil, soybean oil, wheatgerm oil, walnut oil, Oleyl Erucate and mixtures thereof.

Formulations preferred according to the invention comprise the components A) to E) in a weight ratio of the sum of components A) to D) to component E) of from 1:1.1 to 1:10, preferably from 1:1.5 to 1:5, particularly preferably from 1:2 to 1:4.

Structured formulations preferred accordingly according to the invention comprise compositions according to the invention specified above as being preferred according to the invention.

Preferred formulations according to the invention comprise in total the components A) to D) in an amount of from 5% by weight to 35% by weight, preferably 8% by weight to 25% by weight, particularly preferably 11% by weight to 20% by weight, where the percentages by weight refer to the total formulation.

Preferred formulations according to the invention comprise in total the components A) to C) in an amount of from 7% by weight to 16% by weight, where the percentages by weight refer to the total formulation.

The formulations according to the invention are preferably aqueous formulations which preferably comprise water in an amount of from 5% by weight to 80% by weight, preferably 20% by weight to 75% by weight, particularly preferably 30% by weight to 60% by weight, where the percentages by weight refer to the total formulation.

The formulations according to the invention are in particular cosmetic care and cleansing formulations, in particular for skin and skin appendages.

The term "care formulation" is here understood to mean a formulation which satisfies the purpose of restoring an object to its original form, of reducing or avoiding the effects of external influences (e.g., time, light, temperature, pressure, soiling, chemical reaction with other reactive compounds that come into contact with the object) such as ageing, soiling, material fatigue, bleaching or even of improving desired positive properties of the object.

Formulations according to the invention thus include liquid soaps, shower gels, oil baths, make-up removers or shampoos, foam baths, hair shampoos, 2-in-1 shampoos, hair rinses, permanent wave and neutralizing solutions, hair colouring shampoos, hair-setting compositions, hair treatments, hair styling preparations, blowing-drying lotions, foam setting compositions, leave-in conditioners, hair smoothing compositions, shine improving compositions and compositions for colouring the hair.

Cosmetic care and cleansing formulations according to the invention can for example comprise at least one additional component selected from the group of nonionic surfactants, emollients, emulsifiers, thickeners/viscosity regulators/stabilizers, antioxidants, hydrotropes (or polyols), solids and fillers, pearlescence additives, deodorant and antiperspirant active ingredients, insect repellents, self-tanning agents, preservatives, conditioners, perfumes, dyes, cosmetic active ingredients, care additives, superfatting agents, and solvents.

Substances which can be used as exemplary representatives of the individual groups are known to the person skilled in the art and can be found for example in EP2273966A1. This patent application is herewith incorporated as reference and thus forms part of the disclosure.

As regards further optional components and the amounts of these components used, reference is made expressly to the relevant handbooks known to the person skilled in the art, e.g., K. Schrader, "Grundlagen and Rezepturen der Kosmetika" [Fundamentals and Formulations of Cosmetics], 2nd edition, pages 329 to 341, Hüthig Buch Verlag Heidelberg.

The amounts of the particular additives are governed by the intendd use.

Typical guide formulations for the respective applications are known prior art and are contained, for example, in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

The present invention further provides a process for preparing structured formulations, comprising the steps:
  1) provision of a composition according to the invention
  2) mixing of the composition according to the invention with E) at least one cosmetic oil to give a structured formulation comprising the oil in an amount of from 11% by weight to 74% by weight, preferably 16% by weight to 60% by weight, particularly preferably 21% by weight to 55% by weight, where the percentages by weight for the cosmetic oil refer to the total formulation.

The process according to the invention is correspondingly preferably carried out with compositions according to the invention specified above as being preferred, and with components E) specified above as being preferred.

Processes preferred according to the invention are carried out with compositions according to the invention which additionally comprise a solvent such as, for example, water and/or propylene glycol, dipropylene glycol, ethanol, isopropanol, glycerol, in particular water, preferably in an amount of from 20% by weight to 85% by weight, preferably from 30% by weight to 70% by weight, particularly preferably from 40% by weight to 50% by weight, based on the total composition used in process step 1).

According to the invention, the process according to the invention is preferably carried out such that amounts of components A) to D) of from 5% by weight to 35% by weight, preferably 8% by weight to 25% by weight, particularly preferably 11% by weight to 20% by weight, are present in the resulting formulation, where the percentages by weight refer to the total formulation.

According to the invention, the process according to the invention is preferably carried out with amounts of components A) to E) in a weight ratio of the sum of components A) to D) to component E) of from 1:1.1 to 1:10, preferably from 1:1.5 to 1:5, particularly preferably from 1:2 to 1:4.

Process step 2) of the process according to the invention preferably comprises an emulsification of the components present.

In a preferred process according to the invention, water is present in an amount of from 5% by weight to 80% by weight, preferably 20% by weight to 75% by weight, particularly preferably 30% by weight to 60% by weight, where the percentages by weight refer to the total formulation obtained by the process according to the invention.

An alternative process according to the invention for preparing the structured formulations according to the invention, which constitutes a further subject of the present invention, comprises the steps:
  a) provision of a composition comprising
    B) 15 parts by weight to 40 parts by weight, preferably 22 parts by weight to 32 parts by weight, particularly preferably 23 parts by weight to 28 parts by weight, of at least one amphoteric surfactant,
    C) 15 parts by weight to 40 parts by weight, preferably 22 parts by weight to 32 parts by weight, particularly preferably 23 parts by weight to 28 parts by weight, of at least one anionic surfactant, and
    D) 0 parts by weight to 15 parts by weight, preferably 5 parts by weight to 12 parts by weight, particularly preferably 7 parts by weight to 10 parts by weight, of at least one hydrophobic thickener,
  b) adding and mixing the components A) and E) to the composition from process step a)
    A) 20 parts by weight to 67 parts by weight, preferably 25 parts by weight to 57 parts by weight, particularly preferably 33 parts by weight to 47 parts by weight, of at least one substance selected from dialkyl sulfosuccinates and dialkyl methylsulfosuccinates, and
    E) at least one cosmetic oil in an amount of from 11% by weight to 74% by weight, preferably 16% by weight to 60% by weight, particularly preferably 21% by weight to 55% by weight, where the percentages by weight for the cosmetic oil refer to the total formulation to be obtained, and
where the sum of the parts by weight of components A) to D) gives 100 parts by weight.

The components A) and E) can be added according to the invention in process step b) in any desired order. It is possible to add firstly E), then A) or firstly A), then E). The components A) and E) can also be at least partially mixed and then be added according to the invention at least partially in the form of a mixture in process step b).

The components A) to E) used in the alternative process according to the invention correspond to the components present in the structured formulations according to the invention. According to the invention, the process according to the invention is preferably correspondingly carried out with components A) to D) of the compositions according to the invention specified above as being preferred according to the invention, and also with component E) of the structured formulations according to the invention specified above as being preferred.

According to the invention, the alternative process according to the invention is preferably carried out in such a way that amounts of the components A) to D) of from 5% by weight to 35% by weight, preferably 8% by weight to 25% by weight, particularly preferably 11% by weight to 20% by weight, are present in the resulting formulation, where the percentages by weight refer to the total formulation.

According to the invention, the alternative process according to the invention is preferably carried out with amounts of components A) to E) in a weight ratio of the sum of components A) to D) to component E) of from 1:1.1 to 1:10, preferably from 1:1.5 to 1:5, particularly preferably from 1:2 to 1:4.

Process step b) of the alternative process according to the invention preferably comprises an emulsification of the components present.

In a preferred alternative process according to the invention, water is present in an amount of from 5% by weight to 80% by weight, preferably 20% by weight to 75% by weight, particularly preferably 30% by weight to 60% by weight, where the percentages by weight refer to the total formulation obtained by the process according to the invention.

The examples listed below describe the present invention by way of example, without any intention of restricting the invention, the scope of application of which is apparent from the entirety of the description and the claims, to the embodiments specified in the examples.

EXAMPLES

Examples 1 to 34

Formulations with a High Oil Content

| Example | Component A | Component C | Component B | Component D | Component E | Water |
|---|---|---|---|---|---|---|
| 1 | 9% Diethylhexyl Sodium Sulfosuccinate | 3% Sodium Laureth Sulfate | 3% Cocamidopropyl Betaine | 0 | 11% Caprylic/Capric Triglyceride | ad 100% |
| 2 | 9% Diethylhexyl Sodium Sulfosuccinate | 3% Disodium Laureth Sulfosuccinate | 3% Cocamidopropyl Betaine | 0 | 11% Caprylic/Capric Triglyceride | ad 100% |
| 3 | 9% Diethylhexyl Sodium Sulfosuccinate | 3% Disodium PEG-4 Cocamido MIPA-Sulfosuccinate | 3% Cocamidopropyl Betaine | 0 | 11% Caprylic/Capric Triglyceride | ad 100% |
| 4 | 9% Diethylhexyl Sodium Sulfosuccinate | 3% Sodium Laureth Sulfate | 3% Cocamidopropyl Betaine | 0 | 21% Caprylic/Capric Triglyceride | ad 100% |
| 5 | 9% Diethylhexyl Sodium Sulfosuccinate | 3% Sodium Laureth Sulfate | 3% Capryl/Capramidopropyl Betaine | 0 | 21% Caprylic/Capric Triglyceride | ad 100% |
| 6 | 9% Diethylhexyl Sodium Sulfosuccinate | 3% Sodium Laureth Sulfate | 3% Coco-Betaine | 0 | 21% Caprylic/Capric Triglyceride | ad 100% |
| 7 | 9% Diethylhexyl Sodium Sulfosuccinate | 3% Sodium Laureth Sulfate | 3% Sodium Cocoamphoacetate | 0 | 21% Caprylic/Capric Triglyceride | ad 100% |
| 8 | 9% Diethylhexyl Sodium Sulfosuccinate | 3% Disodium Laureth Sulfosuccinate | 3% Sodium Cocoamphoacetate | 0 | 21% Caprylic/Capric Triglyceride | ad 100% |
| 9 | 9% Diethylhexyl Sodium Sulfosuccinate | 3% Disodium PEG-5 Laureth Sulfosuccinate; Capryl/Capramidopropyl Betaine | 3% Sodium Cocoamphoacetate | 0 | 10% Caprylic/Capric Triglyceride | ad 100% |
| 10 | 9% Diethylhexyl Sodium Sulfosuccinate | 3% Sodium Laureth Sulfate | 3% Cocamidopropyl Betaine | 0 | 21% C12-15 Alkyl Benzoate | ad 100% |
| 11 | 9% Diethylhexyl Sodium Sulfosuccinate | 3% Sodium Laureth Sulfate | 3% Cocamidopropyl Betaine | 0 | 21% Triisostearin | ad 100% |
| 12 | 9% Diethylhexyl Sodium Sulfosuccinate | 3% Sodium Laureth Sulfate | 3% Cocamidopropyl Betaine | 0 | 21% soybean oil | ad 100% |
| 13 | 9% Diethylhexyl Sodium Sulfosuccinate | 3% Sodium Laureth Sulfate | 3% Cocamidopropyl Betaine | 0 | 21% *Helianthus Annuus* Seed Oil | ad 100% |
| 14 | 9% Diethylhexyl Sodium Sulfosuccinate | 3% Disodium Lauryl Sulfosuccinate | 3% Cocamidopropyl Betaine | 0 | 21% Oleyl Erucate | ad 100% |
| 15 | 9% Diethylhexyl Sodium Sulfosuccinate | 3% Sodium Lauryl Sulfate | 3% Cocamidopropyl Betaine | 0 | 21% Oleyl Erucate | ad 100% |

| Example | Component A | Component C | Component B | Component D | Component E | Water |
|---|---|---|---|---|---|---|
| 16 | 9% Diethylhexyl Sodium Sulfosuccinate | 3% Sodium Laureth Sulfate | 3% Cocamidopropyl Betaine | 1% Cocamide MEA | 21% Oleyl Erucate | ad 100% |
| 17 | 9% Diethylhexyl Sodium Sulfosuccinate | 3% Sodium Laureth Sulfate | 3% Cocamidopropyl Betaine | 1% Cocamide DEA | 21% Oleyl Erucate | ad 100% |
| 18 | 9% Diethylhexyl Sodium Sulfosuccinate | 3% Disodium Laureth Sulfosuccinate | 3% Cocamidopropyl Betaine | 1% Cocamide MEA | 21% Oleyl Erucate | ad 100% |
| 19 | 8% Diethylhexyl Sodium Sulfosuccinate | 3% Sodium Laureth Sulfate | 3% Cocamidopropyl Betaine | 1% Cocamide DEA | 40% Oleyl Erucate | ad 100% |
| 20 | 7% Diethylhexyl Sodium Sulfosuccinate | 3% Sodium Laureth Sulfate | 3% Cocamidopropyl Betaine | 1% Cocamide MEA | 40% Oleyl Erucate | ad 100% |
| 21 | 5% Diethylhexyl Sodium Sulfosuccinate | 3% Sodium Laureth Sulfate | 3% Cocamidopropyl Betaine | 1% Cocamide MEA | 50% Oleyl Erucate | ad 100% |
| 22 | 5% Diethylhexyl Sodium Sulfosuccinate | 3% Sodium Laureth Sulfate | 5% Cocamidopropyl Betaine | 1% Cocamide MEA | 50% *Helianthus Annuus* Seed Oil | ad 100% |
| 23 | 5% Diethylhexyl Sodium Sulfosuccinate | 3% Sodium Laureth Sulfate | 3% Cocamidopropyl Betaine | 1% Cocamide MEA | 50% *Helianthus Annuus* Seed Oil | ad 100% |
| 24 | 5% Diethylhexyl Sodium Sulfosuccinate | 3% Sodium Laureth Sulfate | 3% Cocamidopropyl Betaine | 1% Cocamide MEA | 50% soybean oil | ad 100% |
| 25 | 5% Diethylhexyl Sodium Sulfosuccinate | 3% Sodium Laureth Sulfate | 3% Cocamidopropyl Betaine | 1% Cocamide MEA | 50% *Helianthus Annuus* Seed Oil | ad 100% |
| 26 | 5% Diethylhexyl Sodium Sulfosuccinate | 3% Disodium Laureth Sulfosuccinate | 3% Cocamidopropyl Betaine | 1% Cocamide MEA | 50% *Helianthus Annuus* Seed Oil | ad 100% |
| 27 | 3% Diethylhexyl Sodium Sulfosuccinate | 3% Sodium Laureth Sulfate | 3% Cocamidopropyl Betaine | 0 | 50% *Helianthus Annuus* Seed Oil | ad 100% |
| 28 | 4% Diethylhexyl Sodium Sulfosuccinate | 3% Sodium Laureth Sulfate | 3% Cocamidopropyl Betaine | 0 | 50% Oleyl Erucate | ad 100% |
| 29 | 4% Diethylhexyl Sodium Sulfosuccinate | 3% Sodium Laureth Sulfate | 3% Cocamidopropyl Betaine | 1% Cocamide MEA | 50% Oleyl Erucate | ad 100% |

| Example | Component A | Component C | Component B | Component D | Component E | Additive | Water |
|---|---|---|---|---|---|---|---|
| 30 | 9% Diethylhexyl Sodium Sulfosuccinate | 3% Sodium Laureth Sulfate | 3% Cocamido-propyl Betaine | 0 | 21% Caprylic/-Capric Triglyceride | 0.2% Polyquaternium-10 | ad 100% |
| 31 | 8% Diethylhexyl Sodium Sulfosuccinate | 3% Sodium Laureth Sulfate | 3% Cocamido-propyl Betaine | 0 | 21% Caprylic/-Capric Triglyceride | 0.2% Polyquaternium-10 | ad 100% |
| 32 | 9% Diethylhexyl Sodium Sulfosuccinate | 3% Sodium Laureth Sulfate | 3% Cocamido-propyl Betaine | 0 | 21% Caprylic/-Capric Triglyceride | 1% Cetrimonium Chloride | ad 100% |

-continued

| Example | Component A | Component C | Component B | Component D | Component E | Additive | Water |
|---|---|---|---|---|---|---|---|
| 33 | 3% Diethylhexyl Sodium Sulfosuccinate | 3% Sodium Laureth Sulfate | 3% Cocamido-propyl Betaine | 1% Cocamide MEA | 50% *Helianthus Annuus* Seed Oil | 0.2% Polyquaternium-10 | ad 100% |
| 34 | 3% Diethylhexyl Sodium Sulfosuccinate | 3% Disodium Laureth Sulfosuccinate | 3% Cocamido-propyl Betaine | 1% Cocamide MEA | 50% *Helianthus Annuus* Seed Oil | 0.2% Polyquaternium-10 | ad 100% |

Example 35

Technical Foam Measurements

SITA R-2000 Foam Tester:

To evaluate the foam properties and in particular the foamability, tests were carried out with the Sita foam tester (SITA R-2000 Foam Tester, SITA Messtechnik GmbH, Germany). For this, formulations according to the invention were tested compared to a market product, namely the comparative example "DG Deeply Moisturizing Body Wash" (PA) according to the prior art. The "DG Deeply Moisturizing Body Wash" includes a structured composition according to WO 2008118381.

Processing was carried out at T=30° C., with water of hardness 10° dH (German hardness), at a pH~6 and with a rotational speed of 1500 rpm.

The table contains the foam heights (in ml) after different times (10-100 sec) of formulations according to the invention which all comprise 3% Sodium Laureth Sulfate, 3% Cocamidopropyl Betaine, 1% Cocamide MEA and 50% sunflower oil and a variable proportion of Diethylhexyl Sodium Sulfosuccinate.

|  | 10 sec | 20 sec | 30 sec | 40 sec | 50 sec | 60 sec | 70 sec | 80 sec | 90 sec | 100 sec |
|---|---|---|---|---|---|---|---|---|---|---|
| 183 | 660.6 | 944.4 | 1019.6 | 1053 | 1069.6 | 1086.2 | 1108.4 | 1109.4 | 1108.4 | 1108.4 |
| 188 | 650.4 | 938.6 | 1023.8 | 1057.8 | 1074.2 | 1089.2 | 1115.6 | 1115.6 | 1115.2 | 1114.6 |
| 187 | 603 | 927 | 1017 | 1057 | 1078 | 1094 | 1112 | 1112 | 1111 | 1111 |
| 201 | 336.8 | 529.4 | 763.4 | 933.2 | 1018 | 1058.2 | 1078.8 | 1102.6 | 1102.2 | 1101.4 |
| DG Body (PA) | 183.2 | 275.4 | 359.6 | 443.6 | 520.2 | 597.2 | 673 | 748.2 | 818.6 | 851 |

The results show firstly that the foam heights of the compositions according to the invention are significantly superior to those according to the prior art.

Moreover, it was able to be shown that as a result of a larger amount of Diethylhexyl Sodium Sulfosuccinate in the formulations according to the invention, the foam volume can be increased; Diethylhexyl Sodium Sulfosuccinate can thus be considered to be a readily foaming surfactant in the formulation.

| Formulation examples | 183 | 188 | 187 | 201 |
|---|---|---|---|---|
| Texapon ® NSO-IS, BASF Cognis, 28%, (INCI: Sodium Laureth Sulfate) | 10.7% | 10.7% | 10.7% | 10.7% |
| TEGO ® Sulfosuccinate DO 75, Evonik Industries AG, 75% (INCI: Diethylhexyl Sodium Sulfosuccinate; Propylene Glycol) | 12.0% | 9.3% | 6.7% | 4.0% |
| TEGO ® Betaine F 50, Evonik Industries AG, 38%, (INCI: Cocamidopropyl Betaine) | 7.9% | 7.9% | 7.9% | 7.9% |
| REWOMID ® C 212, Evonik Industries AG, 100% (INCI: Cocamide MEA) | 1.0% | 1.0% | 1.0% | 1.0% |
| *Helianthus Annuus* Seed Oil (Buttella sunflower oil, Brökelmann + Co., Hamm, Germany) | 50.0% | 50.0% | 50.0% | 50.0% |
| Water, demineralized | 18.4% | 21.1% | 23.7% | 26.4% |

Since the precise proportion of oil in the prior art formulation was not known, formulations with different amounts of oil (Oleyl Erucate, TEGOS OFT OER) were also compared in the Sita foam test. The formulations each consisted again of 3% Sodium Laureth Sulfate, 3% Cocamidopropyl Betaine, 1% Cocamide MEA and 7% Diethylhexyl Sodium Sulfosuccinate.

|  | 10 sec | 20 sec | 30 sec | 40 sec | 50 sec | 60 sec | 70 sec | 80 sec | 90 sec | 100 sec |
|---|---|---|---|---|---|---|---|---|---|---|
| 205 | 603 | 914.4 | 1007.2 | 1044 | 1067 | 1080.8 | 1088.8 | 1089 | 1089.6 | 1089.4 |
| 213 | 661.6 | 941.8 | 1023.4 | 1058.8 | 1073.2 | 1087 | 1112.2 | 1115.2 | 1114.4 | 1113.6 |
| 214 | 653 | 939 | 1024 | 1057 | 1076 | 1091 | 1116 | 1117 | 1117 | 1116 |
| DG Body (PA) | 183.2 | 275.4 | 359.6 | 443.6 | 520.2 | 597.2 | 673 | 748.2 | 818.6 | 851 |

It was found that the formulations according to the invention exhibit greater foam volumes than the formulation according to the prior art after a shorter time irrespective of the proportion of oil.

| Formulation examples | 205 | 213 | 214 |
|---|---|---|---|
| Texapon ® NSO-IS, BASF Cognis, 28%, (INCI: Sodium Laureth Sulfate) | 10.7% | 10.7% | 10.7% |
| TEGO ® Sulfosuccinate DO 75, Evonik Industries AG, 75% (INCI: Diethylhexyl Sodium Sulfosuccinate; Propylene Glycol) | 9.3% | 9.3% | 9.3% |
| TEGO ® Betaine F 50, Evonik Industries AG, 38%, (INCI: Cocamidopropyl Betaine) | 7.9% | 7.9% | 7.9% |
| REWOMID ® C 212, Evonik Industries AG, 100% (INCI: Cocamide MEA) | 1.0% | 1.0% | 1.0% |
| TEGOSOFT ® OER, Evonik Industries AG, 100% (INCI: Oleyl Erucate) | 50.0% | 40.0% | 30.0% |
| Water, demineralized | 21.1% | 31.1% | 41.1% |

Foam Test in Measuring Cylinders

Three screwable and connected 250 ml measuring cylinders were filled with 10 grams of formulation and 20 g of water. By stifling with a glass rod, the thorough mixing of the formulations and the water was ensured. After the measuring cylinders had been closed, the set up was shaken by hand until a volume of 250 ml (foam and liquid) was reached in one of the measuring cylinders. The temperature during this experiment was 23° C. The apparatus was then placed onto a horizontal surface; after 30 seconds, a picture was taken in order to document the foam volumes. The formulations were either formulations which were prepared with a surfactant mixture according to the prior art, or formulations according to the invention. The table below and FIG. 1 summarize the results of the foam test in the cylinder.

| Formulation examples | BW004 | 235 | 236 |
|---|---|---|---|
| Texapon ® NSO-IS, BASF Cognis, 28%, (INCI: Sodium Laureth Sulfate) | — | 10.7% | 14.3% |
| TEGO ® Sulfosuccinate DO 75, Evonik Industries AG, 75% (INCI: Diethylhexyl Sodium Sulfosuccinate; Propylene Glycol) | — | 12.0% | 9.3% |
| TEGO ® Betaine F 50, Evonik Industries AG, 38%, (INCI: Cocamidopropyl Betaine) | — | 7.9% | 10.5% |
| REWOMID ® C 212, Evonik Industries AG, 100% (INCI: Cocamide MEA) | — | 1.0% | 1.0% |
| Miracare 365/N, Rhodia, 40% (INCI: Water, Sodium Trideceth Sulfate, Sodium Lauroamphoacetate, Cocamide MEA, Sodium Chloride, Methylisothiazolinone | 35.0% | — | — |
| Helianthus Annuus Seed Oil (Buttella sunflower oil, Brökelmann + Co., Hamm, Germany) | 27.0% | 27.0% | 27.0% |
| Hydroxypropyl Guar Hydroxypropyltrimonium Chloride (Jaguar C-162, Rhodia, 100%) | 0.1% | 0.1% | 0.1% |
| Sodium chloride solution, 20% by weight in water (sodium chloride, Merck, 99.9%) | 12.5% | — | — |
| Water, demineralized | 25.4% | 41.3% | 37.8% |
| Foam volume | 160 ml | 250 ml | 200 ml |

Figure 1:
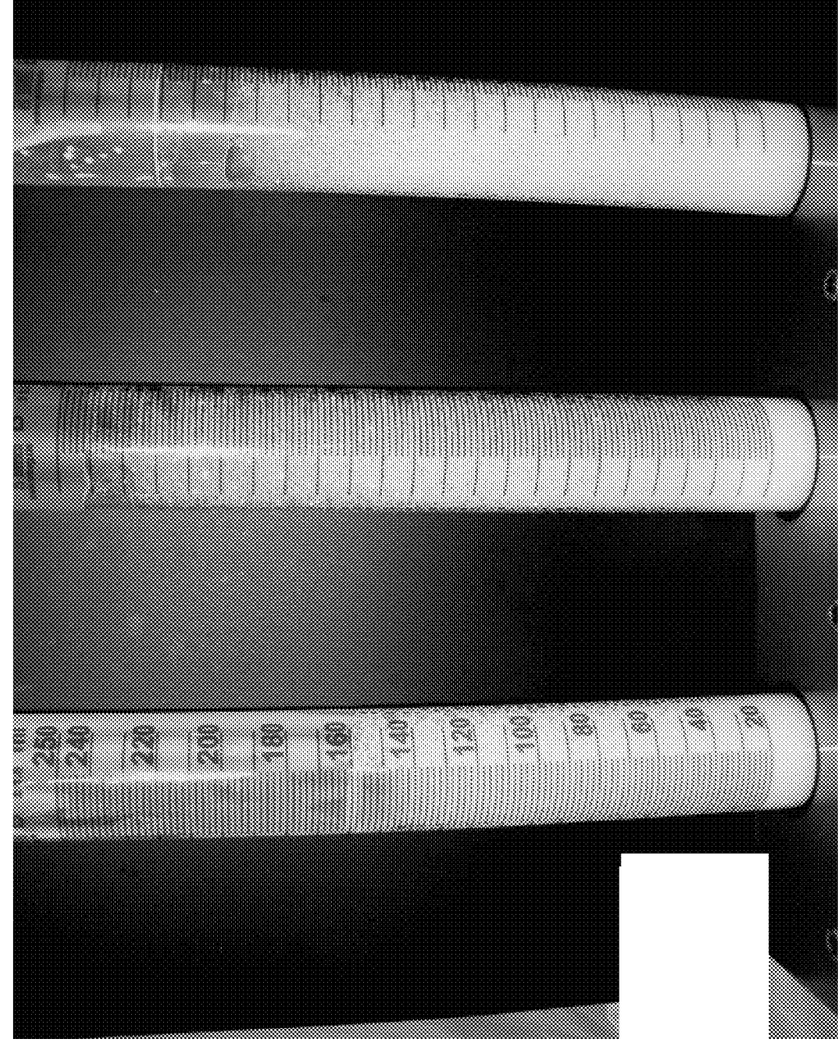
FIG. 1, shows a foam test in a measuring cylinder including a formulation (Left (BW004)) comprising surfactant system according to the prior art; and formulations according to the present invention middle (235) and right (236)

The results of the foam test in the measuring cylinder in FIG. 1 show that the formulations according to the invention are better foaming than formulations according to the prior art. Moreover, it was surprisingly shown that formulations according to the invention with a higher proportion of Diethylhexyl Sodium Sulfosuccinate can be considered to be readily foaming surfactant mixtures.

Example 36

Improved Sensory Foam Properties of the Formulations According to the Invention Compared to the Prior Art To evaluate the foam properties and the skin care performance of the formulations according to the invention, a sensory handwashing test was carried out compared to a market product, namely the comparative example "DG Deeply Moisturizing Body Wash" (PA) according to the prior art. The "DG Deeply Moisturizing Body Wash" includes a structured composition according to WO 2008118381.

A group consisting of 10 trained test personnel washed their hands in a defined manner and assessed foam properties and skin feel using a grading scale from 1 (poor) to 5 (very good).

The compositions of the formulations according to the invention are listed in Table 01:

TABLE 01

Test formulations for the handwashing test:

| Formulation examples | 149 | 153 | 160 |
|---|---|---|---|
| Texapon ® NSO-IS, BASF Cognis, 28%, (INCI: Sodium Laureth Sulfate) | 10.7% | | |
| REWOPOL ® SB FA 30 B, Evonik Industries AG, 40% (INCI: Disodium Laureth Sulfosuccinate) | | 7.5% | |
| REWOPOL ® SB C 55, Evonik Industries AG, 40% (INCI: Disodium PEG-5 Laurylcitrate Sulfosuccinate; Capryl/Capramidopropyl Betaine) | | | 7.5% |
| TEGO ® Sulfosuccinate DO 75 Diethylhexyl Sodium Sulfosuccinate, Evonik Industries AG, 75% (INCI: Diethylhexyl Sodium Sulfosuccinate; Propylene Glycol) | 12.0% | 12.0% | 12.0% |
| TEGO ® Betaine F 50, Evonik Industries AG, 38%, (INCI: Cocamidopropyl Betaine) | 7.9% | 7.9% | 7.9% |
| REWOMID ® C 212, Evonik Industries AG, 100% (INCI: Cocamide MEA) | 1.0% | 1.0% | 1.0% |
| TEGOSOFT ® OER, Evonik Industries AG, 100% (INCI: Oleyl Erucate) | 21.0% | 21.0% | 21.0% |
| Water, demineralized | 47.4% | 50.6% | 50.6% |

The sensory test results are summarized in Table 02.

TABLE 02

Results of the handwashing test:

| Test formulation | 149 | 153 | 160 | PA |
|---|---|---|---|---|
| Foaming behaviour | 3.1 | 3.4 | 2.3 | 1.3 |
| Foam volume | 2.9 | 2.5 | 2.1 | 1.0 |
| Skin feel during washing | 3.1 | 3.2 | 3.1 | 4.1 |
| Foam creaminess | 2.1 | 2.2 | 2.3 | 1.1 |
| Rinseability | 3.4 | 3.4 | 3.5 | 2.3 |
| Skin smoothness | 1.9 | 1.8 | 2.3 | 2.6 |
| Skin softness | 2.6 | 2.6 | 2.8 | 3.1 |
| Skin smoothness after 3 min | 3.8 | 3.3 | 3.6 | 3.8 |
| Skin softness after 3 min | 3.6 | 3.5 | 3.8 | 3.8 |

It is evident from the test results in Table 02 that the formulations according to the invention are superior in many application properties compared to the PA comparison formulation according to the prior art. Against this background, the results of the formulations according to the invention can be designated as very good and exhibit a considerable improvement compared to the prior art.

It is evident from the measurement values that the formulations according to the invention led in particular to a significant improvement, specifically as regards foaming behaviour, foam volume, foam creaminess and rinseability.

Further formulation examples:

| | 37a | 37b | 37c | 37d | 37e | 37f | 37g |
|---|---|---|---|---|---|---|---|
| Water | ad 100% | | | | | | |
| Sodium Laureth Sulfate | 3.0% | 3.0% | 3.0% | 3.0% | 3.0% | 3.0% | 3.0% |
| Cocamidopropyl Betaine | 3.0% | 3.0% | 3.0% | 3.0% | 3.0% | 3.0% | 3.0% |
| Cocamide MEA | 1.0% | 1.0% | 1.0% | 1.0% | 1.0% | 0.0% | 0.0% |
| Diethylhexyl Sodium Sulfosuccinate | 9.0% | 9.0% | 9.0% | 8.0% | 7.0% | 9.0% | 9.0% |
| Capryl/Capric TriglycerideCaprylic/Capric Triglyceride | 10.0% | 20.0% | 30.0% | 40.0% | 50.0% | 20.0% | 50.0% |

| | 38a | 38b | 38c | 38d | 38e | 38f | 38g |
|---|---|---|---|---|---|---|---|
| Water | ad 100% | | | | | | |
| Sodium Laureth Sulfate | 3.0% | 3.0% | 3.0% | 3.0% | 5.0% | 3.0% | 3.0% |
| Cocamidopropyl Betaine | 3.0% | 3.0% | 3.0% | 3.0% | 3.0% | 3.0% | 3.0% |
| Cocamide MEA | 1.0% | 1.0% | 1.0% | 1.0% | 1.0% | 0.0% | 0.0% |
| Diethylhexyl Sodium Sulfosuccinate | 4.0% | 5.0% | 7.0% | 9.0% | 5.0% | 5.0% | 7.0% |
| Oleyl Erucate | 50.0% | 50.0% | 50.0% | 50.0% | 50.0% | 50.0% | 50.0% |

| | 39a | 39b | 39c | 39d | 39e | 39f | 39g |
|---|---|---|---|---|---|---|---|
| Water | ad 100% | | | | | | |
| Sodium Laureth Sulfate | 3.0% | 3.0% | 3.0% | 3.0% | 3.0% | 3.0% | 3.0% |
| Cocamidopropyl Betaine | 3.0% | 3.0% | 3.0% | 3.0% | 3.0% | 3.0% | 3.0% |
| Cocamide MEA | 0.0% | 0.0% | 0.0% | 0.0% | 0.0% | 1.0% | 1.0% |
| Diethylhexyl Sodium Sulfosuccinate | 5.0% | 5.0% | 5.0% | 5.0% | 5.0% | 5.0% | 5.0% |
| Oleyl Erucate | 40.0% | 40.0% | 40.0% | 40.0% | 40.0% | 40.0% | 40.0% |
| Sodium Cocoyl Glutamate | 1.0% | 1.0% | 1.0% | 0.0% | 0.0% | 0.0% | 0.0% |
| Cocamide DEA | 0.0% | 0.5% | 1.0% | 0.0% | 0.0% | 0.0% | 0.0% |

| | 40a | 40b | 40c | 40d | 40e | 40f | 40g |
|---|---|---|---|---|---|---|---|
| Water | ad 100% | | | | | | |
| Sodium Laureth Sulfate | 3.0% | 3.0% | 3.0% | 3.0% | 3.0% | 3.0% | 3.0% |

-continued

| | | | | | | | |
|---|---|---|---|---|---|---|---|
| Cocamidopropyl Betaine | 3.0% | 3.0% | 3.0% | 3.0% | 3.0% | 3.0% | 3.0% |
| Cocamide MEA | 1.0% | 1.0% | 1.0% | 1.0% | 1.0% | 1.0% | 1.0% |
| Diethylhexyl Sodium Sulfosuccinate | 5.0% | 5.0% | 5.0% | 5.0% | 5.0% | 5.0% | 5.0% |
| Oleyl Erucate | 40.0% | 30.0% | 40.0% | 40.0% | 40.0% | 40.0% | 40.0% |
| Glycerin | 0.0% | 0.0% | 5.0% | 0.0% | 0.0% | 0.0% | 0.0% |
| Polyquaternium-10 | 0.0% | 0.0% | 0.0% | 0.5% | 0.0% | 0.0% | 0.0% |
| Hydroxypropyl Guar Hydroxypropyltrimonium Chloride | 0.0% | 0.0% | 0.0% | 0.0% | 0.5% | 0.0% | 0.5% |
| Silicone Quaternium-22 | 0.0% | 0.0% | 0.0% | 0.0% | 0.0% | 0.5% | 0.0% |
| Dimethicone | 0.0% | 0.0% | 0.0% | 0.5% | 0.0% | 0.0% | 0.0% |
| Amodimethicone | 0.0% | 0.0% | 0.0% | 0.0% | 0.0% | 0.0% | 0.5% |
| *Argania Spinosa* Oil | 0.0% | 10.0% | 0.0% | 0.0% | 0.0% | 0.0% | 0.0% |

| | 41a | 41b | 41c | 41d | 41e | 41f | 41g |
|---|---|---|---|---|---|---|---|
| Water | | | | ad 100% | | | |
| Sodium Laureth Sulfate | 3.0% | 3.0% | 3.0% | 3.0% | 3.0% | 3.0% | 3.0% |
| Cocamidopropyl Betaine | 3.0% | 3.0% | 3.0% | 3.0% | 3.0% | 3.0% | 3.0% |
| Cocamide MEA | 0.0% | 1.0% | 1.0% | 1.0% | 1.0% | 1.0% | 1.0% |
| Diethylhexyl Sodium Sulfosuccinate | 5.0% | 5.0% | 5.0% | 5.0% | 5.0% | 5.0% | 5.0% |
| *Prunus Amygdalus Dulcis* Oil | 20.0% | 0.0% | 10.0% | 0.0% | 0.0% | 10.0% | 0.0% |
| *Olea Europaea* Fruit Oil | 5.0% | 5.0% | 0.0% | 0.0% | 20.0% | 10.0% | 0.0% |
| *Butyrospermum Parkii* Butter Extract | 5.0% | 20.0% | 5.0% | 0.0% | 10.0% | 0.0% | 0.0% |
| *Persea Gratissima* Oil | 0.0% | 0.0% | 10.0% | 30.0% | 0.0% | 20.0% | 0.0% |
| Isostearamide MIPA | 1.0% | 0.0% | 0.0% | 0.0% | 0.0% | 0.0% | 0.0% |
| Zinc Pyrithione | 0.0% | 0.1% | 0.0% | 0.0% | 0.0% | 0.0% | 0.0% |
| Benzophenone-4 | 0.0% | 0.1% | 0.1% | 0.1% | 0.1% | 0.0% | 0.1% |
| Tetrasodium EDTA | 0.1% | 0.1% | 0.0% | 0.1% | 0.1% | 0.0% | 0.0% |
| Caffeine | 0.0% | 0.1% | 0.1% | 0.0% | 0.0% | 0.0% | 0.0% |
| Hydrolyzed Keratin | 0.0% | 0.0% | 0.1% | 0.0% | 0.0% | 0.1% | 0.2% |
| Panthenol | 0.1% | 0.1% | 0.1% | 0.1% | 0.1% | 0.1% | 0.0% |

| | 42a | 42b | 42c | 42d | 42e | 42f | 42g |
|---|---|---|---|---|---|---|---|
| Water | | | | ad 100% | | | |
| Sodium Laureth Sulfate | 0.0% | 0.0% | 3.0% | 3.0% | 0.0% | 0.0% | 0.0% |
| Cocamidopropyl Betaine | 3.0% | 3.0% | 0.0% | 0.0% | 0.0% | 3.0% | 3.0% |
| Cocamide MEA | 0.0% | 1.0% | 1.0% | 1.0% | 1.0% | 1.0% | 1.0% |
| Diethylhexyl Sodium Sulfosuccinate | 5.0% | 5.0% | 5.0% | 5.0% | 5.0% | 5.0% | 5.0% |
| Sodium Lauryl Sulfate | 3.0% | 0.0% | 0.0% | 0.0% | 0.0% | 3.0% | 3.0% |
| Ammonium Laureth Sulfate | 0.0% | 3.0% | 3.0% | 0.0% | 0.0% | 0.0% | 0.0% |
| Capryl/Capramidopropyl Betain | 0.0% | 0.0% | 3.0% | 3.0% | 3.0% | 0.0% | 3.0% |
| Disodium Lauryl Sulfosuccinate | 0.0% | 0.0% | 0.0% | 0.0% | 3.0% | 3.0% | 0.0% |
| Disodium PEG-4 Cocamido MIPA-Sulfosuccinate | 0.0% | 0.0% | 0.0% | 0.0% | 0.0% | 0.0% | 3.0% |

| | 43a | 43b | 43c | 43d | 43e | 43f | 43g | 43h | 43i | 43j |
|---|---|---|---|---|---|---|---|---|---|---|
| Water | | | | | ad 100% | | | | | |
| Diethylhexyl Sodium Sulfosuccinate | 10.0% | 7.5% | 6.5% | 6.0% | 9.0% | 7.0% | 9.0% | 6.0% | 8.5% | 6.5% |
| Sodium Laureth Sulfate | 3.5% | 3.0% | 2.5% | — | — | 2.5% | 1.5% | 2.6% | — | — |
| Sodium Lauryl Sulfate | — | — | 0.5% | 3.0% | 3.2% | — | 1.0% | 0.5% | 3.5% | 2.5% |

-continued

|  |  |  |  |  |  |  |  |  |  |  |
|---|---|---|---|---|---|---|---|---|---|---|
| Cocamidopropyl Betaine | — | 3.0% | 3.0% | 2.8% | 4.0% | 3.5% | — | 1.0% | 2.0% | 3.0% |
| Sodium Cocoamphoacetate | 3.0% | — | — | 0.5% | — | — | 3.0% | 2.0% | 3.5% | — |
| Lauryl Glucoside | — | — | — | — | 0.2% | — | — | — | — | — |
| Coco-Glucoside | — | 0.5% | — | — | 0.3% | — | 0.5% | — | — | — |
| Sodium/Disodium Cocoyl Glutamate | — | — | — | — | 0.2% | 1.0% | 1.0% | — | 0.3% | — |
| Stearic Acid | — | — | 0.1% | — | — | — | — | — | — | 0.2% |
| Glycerin | 0.5% | 1.0% | 0.5% | — | 0.3% | 0.4% | 1.0% | 0.4% | 0.4% | 0.2% |
| Polyglyceryl-4 Caprate | — | — | — | 1.0% | — | 0.5% | — | — | — | 0.5% |
| Polyquaternium-10 | — | 0.2% | — | 0.1% | — | — | — | 0.2% | 0.2% | — |
| Hydroxypropyl Guar Hydroxypropyltrimonium Chloride | 0.2% | — | 0.3% | 0.2% | 0.2% | — | 0.2% | 0.1% | — | — |
| Palmitamidopropyl-trimonium Chloride | — | 0.1% | 0.2% | — | — | — | — | — | — | 0.1% |
| Silicone Quaternium-22 | — | — | 0.3% | — | 0.3% | — | — | — | — | — |
| Dimethicone | — | — | — | — | — | — | — | — | 0.1% | — |
| Amodimethicone | — | — | — | 0.5% | — | — | — | 0.5% | — | — |
| *Argania Spinosa* Oil | — | — | 0.2% | 0.1% | 0.1% | — | 0.2% | — | — | — |
| *Glycine Soja* Oil | 22% | — | — | — | 20% | 25% | 25% | 25% | 25% | 25% |
| *Simmondsia Chinensis* (Jojoba) Seed Oil | — | 35% | — | — | — | — | — | 5% | — | — |
| *Prunus Amygdalus Dulcis* Oil | — | — | 40% | — | — | — | — | 5% | 0.5% | — |
| *Olea Europaea* Fruit Oil | — | — | — | 45% | — | — | — | 5% | 0.5% | 20% |
| *Butyrospermum Parkii* Butter Extract | — | — | — | — | 15% | — | — | — | — | — |
| *Persea Gratissima* Oil | — | — | — | — | — | 15% | 2% | — | — | — |
| Hydrogenated Castor Oil | — | — | — | — | — | — | 8% | — | 0.5% | 0.5% |
| Glycol Distearate | — | 0.5% | — | — | 0.5% | — | 0.3% | — | — | — |
| Isostearamide MIPA | 1.0% | — | — | 1.5% | — | — | 0.2% | — | 1.0% | 0.5% |
| Cocamide DEA | — | — | 0.5% | — | — | 1.0% | — | — | — | — |
| Sodium Chloride | 0.3% | — | 0.3% | 0.5% | — | — | — | 0.2% | — | 0.3% |
| PEG-200 Hydrogenated Glyceryl Palmate; PEG-7 Glyceryl Cocoate | 0.2% | — | — | — | — | — | — | — | 0.5% | — |
| Xanthan Gum | — | — | — | — | — | 0.7% | — | — | — | — |
| Cellulose | — | — | — | 0.1% | — | 0.1% | — | 0.2% | 0.1% | — |
| Zinc Pyrithione | — | 0.1% | — | — | — | — | — | — | 0.1% | — |
| Benzophenone-4 | — | 0.1% | 0.1% | 0.1% | 0.1% | — | 0.1% | — | 0.1% | — |
| Tetrasodium EDTA | 0.1% | 0.1% | — | 0.1% | 0.1% | — | — | — | 0.1% | — |
| Hydrolyzed Keratin | — | — | 0.1% | — | — | 0.1% | 0.2% | — | 0.1% | — |
| Creatine | — | 0.3% | — | — | — | — | — | — | — | 0.1% |
| Panthenol | 0.1% | 0.1% | 0.1% | 0.1% | 0.1% | 0.1% | — | 0.1% | 0.1% | 0.1% |
| Citric Acid | | | | | ad pH 5.5 | | | | | |
| Perfumes, Dyes, Preservatives | | | | | q.s. | | | | | |

|  | 44a | 44b | 44c | 44d | 44e | 44f | 44g | 44h | 44i | 44j |
|---|---|---|---|---|---|---|---|---|---|---|
| Water | | | | | ad 100% | | | | | |
| Diethylhexyl Sodium Sulfosuccinate | 9.0% | 4.0% | 3.5% | 8.0% | 4.0% | 8.5% | 4.0% | 6.0% | 8.5% | 9.0% |
| Sodium Laureth Sulfate | 3.0% | 3.0% | — | 2.0% | 1.5% | — | 2.0% | 1.0% | 3.3% | — |
| Sodium C14-16 Olefin Sulfonate | — | — | — | 1.0% | — | 1.5% | — | — | — | — |
| Coco-Betaine | — | 3.0% | — | 0.5% | — | — | — | 1.0% | — | — |
| Cocamidopropyl Betaine | 3.0% | — | 3.0% | 2.5% | 1.0% | 2.5% | — | 1.0% | 3.0% | 2.7% |
| Sodium Cocoamphopropionate | — | — | — | — | 1.0% | 0.5% | 0.7% | — | — | — |
| Disodium Cocoamphodiacetate | — | — | — | 0.5% | — | — | 0.8% | — | — | 0.3% |
| Disodium Laureth Sulfosuccinate | — | — | 3.0% | — | 0.5% | — | 1.0% | 1.0% | — | 3.0% |
| Coco-Glucoside | — | — | — | — | — | — | 0.5% | — | 0.5% | 0.5% |
| Sodium Cocoyl Glutamate | — | — | — | — | — | — | 0.5% | 0.5% | 0.5% | — |
| Sodium Cocoyl Glycinate | — | — | — | — | 1.0% | 1.5% | — | 1.0% | 0.5% | — |
| Sodium Lauroyl Methyl Isethionate | — | — | — | 0.5% | — | 0.5% | — | — | 0.2% | — |
| Sodium Cocoyl Sarcosinate | — | — | — | — | 0.5% | — | 0.2% | 0.3% | — | — |
| Laureth-5 Carboxylic Acid | — | — | — | — | 0.2% | — | — | — | — | — |
| Glycerin | 1.0% | 0.3% | 0.5% | 0.5% | 0.3% | 0.5% | 0.5% | 0.5% | 0.3% | 1.0% |
| PEG-40 Hydrogenated Castor Oil | — | 0.3% | — | — | — | — | — | 0.3% | — | — |
| Polyquaternium-7 | 0.2% | — | — | — | 0.1% | — | 0.2% | — | — | 0.3% |
| Guar Hydroxypropyltrimonium Chloride | — | — | 0.3% | — | 0.2% | — | 0.2% | 0.1% | — | — |

-continued

| Ingredient | 1 | 2 | 3 | 4 | 5 | 6 | 7 | 8 | 9 | 10 |
|---|---|---|---|---|---|---|---|---|---|---|
| Dimethicone | 1.2% | — | — | — | — | 0.5% | — | 0.2% | — | 0.3% |
| Petrolatum | — | — | 4% | 5% | — | 2% | 3% | — | — | 2% |
| *Helianthus Annuus* Seed Oil | 25% | 45% | 20% | 21% | 35% | 15% | — | 15% | — | 10% |
| *Ricinus Communis* Seed Oil | — | 10% | 10% | — | — | 5% | 15% | 10% | 15% | 2% |
| *Olea Europaea* Fruit Oil | — | — | 15% | — | 10% | — | 25% | 10% | 7% | 10% |
| Acrylates/C10-30 Alkyl Acrylate Crosspolymer | — | — | — | — | 0.3% | — | — | 0.3% | 0.2% | — |
| Sodium Hydroxide, 25% | — | — | — | — | 0.5% | — | — | 0.5% | 0.5% | — |
| Cocamide MEA | — | 0.8% | 1.0% | 0.5% | — | 0.2% | 0.6% | — | — | 0.3% |
| Sodium Chloride | 0.2% | — | — | — | — | 0.1% | — | — | 0.2% | 0.5% |
| Propylene Glycol; PEG-55 Propylene Glycol Oleate | — | — | — | — | 0.4% | — | — | — | — | — |
| Sodium Hydroxypropyl Starch Phosphate | — | — | — | — | — | 0.5% | — | — | — | 0.6% |
| Hydroxypropyl Methylcellulose | — | — | — | 0.3% | — | — | 0.3% | — | — | — |
| Dicaprylylether | — | — | 1.0% | — | — | — | 0.4% | — | — | — |
| Cetearyl Alcohol | — | — | — | — | — | — | 0.1% | — | — | 0.2% |
| Benzophenone-4 | — | 0.1% | 0.2% | — | — | — | — | 0.2% | — | 0.1% |
| Salicylic Acid | — | 0.1% | — | — | — | — | 0.1% | — | — | — |
| Octopirox | 0.1% | — | — | 0.1% | — | — | — | — | — | 0.1% |
| Caffeine | — | — | 0.1% | — | 0.1% | — | — | 0.1% | — | 0.1% |
| Benzyl Alcohol | 0.1% | — | — | — | — | 0.1% | — | 0.1% | — | — |
| Hydrolyzed Wheat Protein | — | — | 0.1% | 0.1% | 0.1% | — | 0.2% | 0.1% | — | — |
| Panthenol | 0.1% | 0.1% | — | 0.1% | 0.1% | 0.1% | 0.1% | — | 0.1% | 0.1% |
| Citric Acid | | | | | ad pH 5.3 | | | | | |
| Perfumes, Dyes, Preservatives | | | | | q.s. | | | | | |

List of Raw Materials Used

| INCI | Trade name, company |
|---|---|
| Acrylates/C10-30 Alkyl Acrylate Crosspolymer | TEGO Carbomer 841 SER, Evonik Industries AG, 100% |
| Ammonium Laureth Sulfate | Sulfetal LA, Tschimmer & Schwarz, 28% |
| Amodimethicone | DC 949, Dow Corning, 100% |
| *Argania Spinosa* Oil (*Argania Spinosa* Kernel Oil) | Argan Oil, DSM Nutritional Products Ltd. |
| Benzophenone-4 | Uvinul MS 40, BASF |
| Benzyl Alcohol | Microcare BNA, THOR Personal Care SAS |
| *Butyrospermum Parkii* Butter Extract | Cosmosil 600, International Cosmetic Science Centre |
| Caffeine | Caffeine, Merck KGaA/EMD Chemicals, Inc. |
| Capryl/Capramidopropyl Betaine | TEGO Betaine 810, Evonik Industries AG, 38% |
| Caprylic/Capric Triglyceride | CAPRYLIC/CAPRIC TRIGLYCERIDE, Evonik Industries AG, 100% |
| Cellulose | Arbocel A300, J. Rettenmaier & Söhne |
| Cetearyl Alcohol | TEGO Alkanol 1618, Evonik Industries AG, 100% |
| Citric Acid | Citric Acid USP Granular, DSM Nutritional Products, Inc. |
| Cocamide DEA | REWOMID DC 212 S, Evonik Industries AG, 100% |
| Cocamide MEA | REWOMID D 212, Evonik Industries AG, 100% |
| Cocamidopropyl Betaine | TEGO Betain F 50, Evonik Industries AG, 38% |
| Coco-Glucoside | Plantacare 818 UP, BASF Cognis, 51% |
| Coco-Betaine | TEGO Betaine AB 1214, Evonik Industries AG, 31% |
| Creatine | TEGO Cosmo C 100, Evonik Industries AG, 100% |
| Dicaprylylether | Cetiol OE, BASF Cognis |
| Diethylhexyl Sodium Sulfosuccinate | TEGO Sulfosuccinate DO 75, Evonik Industries AG, 75% |
| Dimethicone | DC 200 Fluid 100 cSt, Dow Corning, 100% |
| Disodium Cocoamphodiacetate | REWOTERIC AM 2 C NM, Evonik Industries AG |
| Disodium Laureth Sulfosuccinate | REWOPOL SB FA 30 B, Evonik Industries AG, 40% |
| Disodium Lauryl Sulfosuccinate | REWOPOL SB F 12 P, Evonik Industries AG, 95% |
| Disodium PEG-4 Cocamido MIPA-Sulfosuccianate | REWOPOL SB Z U, Evonik Industries AG, 50% |
| Glycerin | Glycerol EP, vegetable, Spiga Nord, 99.7% |
| *Glycine Soja* (Soybean) Oil | Cropure Soybean, Croda Europe, Ltd. |
| Glycol Distearate | TEGIN G 1100, Evonik Industries AG, 100% |
| *Helianthus Annuus* (Sunflower) Seed Oil | Buttella sunflower oil, Brökelmann + Co., Hamm, Germany. |
| Hydrogenated Castor Oil | Cutina HR Powder, BASF Personal Care and Nutrition Gmbh |
| Hydrolyzed Keratin | Kerasol, Croda, Inc. |
| Hydrolyzed Wheat Protein | Gluadin WLM, BASF Cognis |
| Hydroxypropyl Guar Hydroxypropyltrimonium Chloride | Jaguar C-162, Rhodia, 100% |
| Hydroxypropyl Methylcellulose | TEGOCEL HPM 50, Evonik Industries AG, 100% |
| Isostearamide MIPA | REWOMID IPP 240, Evonik Industries AG, 100% |
| Laureth-5 Carboxylic Acid | Marlowet 1072, Sasol Germany GmbH |
| Lauryl Glucoside | Plantacare 1200 UP, BASF Cognis, 50% |
| Octopirox | Octopirox, Clariant Intl. Ltd. |
| *Olea Europaea* (Olive) Fruit Oil | Cropure Olive, Croda Europe, Ltd. |
| Oleyl Erucate | TEGOSOFT OER, Evonik Industries AG, 100% |
| Palmitamidopropyltrimonium Chloride | VARISOFT PATC, Evonik Industries AG, 60% |
| Panthenol | D-Panthenol USP, BASF, 100% |
| PEG-200 Hydrogenated Glyceryl Palmate; PEG-7 Glyceryl Cocoate | REWODERM LI S 80, Evonik Industries AG, 100% |
| PEG-40 Hydrogenated Castor Oil | TAGAT CH 40, Evonik Industries AG, 100% |
| *Persea Gratissima* (Avocado) Oil | Cropure Avocado, Croda Europe, Ltd. |
| Petrolatum | Merkur 115, Sasol Wax GmbH |
| Polyglyceryl-4 Caprate | TEGOSOFT PC 41, Evonik Industries AG, 100% |
| Polyquaternium-10 | Polymer JR 400, Amerchol, 100% |

-continued

| INCI | Trade name, company |
|---|---|
| Polyquaternium-7 | Merquat 550, Nalco, 100% |
| Propylene Glycol; PEG-55 Propylene Glycol Oleate | ANTIL 141 Liquid, Evonik Industries AG |
| *Prunus Amygdalus Dulcis* (Sweet Almond) Oil | Cropure Almond, Croda Europe, Ltd. |
| *Ricinus Communis* Seed Oil | Lipovol CO, Lipo Chemicals |
| Salicylic Acid | OriStar SCA, Orient Stars LLC |
| Silicone Quaternium-22 | ABIL T Quat 60, Evonik Industries AG, 65% |
| *Simmondsia Chinensis* (Jojoba) Seed Oil | AEC Jojoba Oil Refined, A & E Connock, Perfumery & Cosmetics Ltd. |
| Sodium C14-16 Olefin Sulfonate | Bioterge AS-40 AOS, Stepan, |
| Sodium Cocoamphoacetate | REWOTERIC AM C, Evonik Industries AG, 32% |
| Sodium Cocoamphopropionate | REWOTERIC AM KSF 40, Evonik Industries AG, 40% |
| Sodium Cocoyl Glutamate | Plantapon ACG HC, BASF Cognis |
| Sodium Cocoyl Glycinate | Hostapon SG, Clariant; Amilite GCS-11, Ajinomoto |
| Sodium Cocoyl Sarcosinate | Crodasinic CS, Croda |
| Sodium/Disodium Cocoyl Glutamate | PERLASTAN SC 25 NKW, Schill&Seilacher, 25%, |
| Sodium Hydroxide | Unichem SOHYD, Universal Preserv-A-Chem, Inc. |
| Sodium Hydroxypropyl Starch Phosphate | Pure-Gel, Grain Processing Corporation |
| Sodium Laureth Sulfate | Texapon NSO, BASF Cognis, 28% |
| Sodium Lauroyl Methyl Isethionate | Iselux, Innospec Active Chemicals |
| Sodium Lauryl Sulfate | Texapon LS 35, BASF Cognis, 30% |
| Stearic Acid | Pristerene 4922, Croda Europe, Ltd. |
| Tetrasodium EDTA | Versene 100, The Dow Chemical Company |
| Xanthan Gum | Keltrol CG-SFT, CP Kelco, 100% |
| Zinc Pyrithione | Microcare ZP, Thor Personal Care SAS |

While the present invention has been shown and described with respect to preferred embodiments thereof, it will be understood by one skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A composition comprising:
   A) 20 parts by weight to 67 parts by weight, of at least one substance selected from dialkyl sulfosuccinates and dialkyl methylsulfosuccinates,
   B) 15 parts by weight to 40 parts by weight, of at least one amphoteric surfactant, and
   C) 15 parts by weight to 40 parts by weight, of at least one anionic surfactant.

2. The composition according to claim 1, wherein the dialkyl sulfosuccinate and/or dialkyl methylsulfosuccinate are selected from the group consisting of dialkyl sulfosuccinates and/or dialkyl methylsulfosuccinates in which the alkyl radicals each have 4 to 24 carbon atoms.

3. The composition according to claim 2, wherein the amphoteric surfactant is selected from alkylbetaines, alkylamidoalkylbetaines, alkyl amphoacetates, alkyl amphodiacetates, alkyl amphopropionates, alkyl amphodipropionates, alkylsultaines, alkylhydroxysultaines, alkylamine oxides, alkyl amphoglycinates, alkyl iminodiacetates, alkyl iminodipropionates, alkyl amphopropylsulfonates, and also alkali metal, alkaline earth metal or ammonium salts of alkyl amphocarboxyglycinates and alkyl amphocarboxypropionates.

4. The composition according to claim 2, wherein the anionic surfactant is selected from alkyl sulfates, alkyl ether sulfates, optionally alkoxylated sulfosuccinates, optionally alkoxylated methylsulfosuccinates, optionally alkoxylated sulfonates, optionally alkoxylated glycinates, optionally alkoxylated glutamates, optionally alkoxylated isethionates, optionally alkoxylated carboxylates, optionally alkoxylated anisates, optionally alkoxylated levulinates, optionally alkoxylated tartrates, optionally alkoxylated lactylates, optionally alkoxylated taurates, optionally alkoxylated alaninates, optionally alkoxylated phosphates, optionally alkoxylated sulfoacetates, optionally alkoxylated sulfosuccinates, optionally alkoxylated sarcosinates and optionally alkoxylated phosphonates.

5. The composition according to claim 1, further comprising:
   D) 0 parts by weight to 15 parts by weight, of at least one hydrophobic thickener.

6. The composition according to claim 5, wherein the hydrophobic thickener is selected from reaction products of at least one fatty acid and/or at least one fatty acid ester, with at least one primary or secondary amine, and cationic surfactants in which, at a pH of 7 and 20° C., at least 90 mol % of the molecules have at least one positively charged group.

7. The composition according to claim 1, further comprising a solvent.

8. A structured formulation comprising:
   a composition according to claim 1, and
   E) at least one cosmetic oil in an amount of from 11% by weight to 74% by weight, where the percentages by weight refer to the total formulation.

9. The structured formulation according to claim 8, wherein components A) to D) are present in an amount of from 5% by weight to 35% by weight, where the percentages by weight refer to the total formulation.

10. The structured formulation according to claim 8, said formulation having a yield point of greater than 0.001 Pa.

11. The structured formulation according to claim 8, wherein the cosmetic oil is selected from silicone oils, functionalized silicones, mineral oils, fatty acid esters, natural oils, animal oils, and mixtures thereof.

12. The structured formulation according to claim 8, wherein said formulation is a cosmetic care and cleansing formulation.

13. A process for preparing structured formulations, said process comprising:
   1) providing a composition comprising
      A) 20 parts by weight to 67 parts by weight, of at least one substance selected from dialkyl sulfosuccinates and dialkyl methylsulfosuccinates,
      B) 15 parts by weight to 40 parts by weight, of at least one amphoteric surfactant, and
      C) 15 parts by weight to 40 parts by weight, of at least one anionic surfactant,
   2) mixing the composition with
      E) at least one cosmetic oil to give a structured formulation comprising the oil in an amount of from 11% by weight to 74% by weight, where the percentages by weight refer to the total formulation.

14. A process for preparing structured formulations, said process comprising:
   a) providing a composition comprising
      B) 15 parts by weight to 40 parts by weight, of at least one amphoteric surfactant,
      C) 15 parts by weight to 40 parts by weight, of at least one anionic surfactant, and D) 0 parts by weight to 15 parts by weight, of at least one hydrophobic thickener,
b) adding and mixing components A) and E) to the composition from process step a)
A) 20 parts by weight to 67 parts by weight, of at least one substance selected from dialkyl sulfosuccinates and dialkyl methylsulfosuccinates, and
E) at least one cosmetic oil in an amount of from 11% by weight to 74% by weight, where the percentages by weight for the cosmetic oil refer to the total formulation to be obtained, and where the sum of the parts by weight of components A) to D) gives 100 parts by weight.

* * * * *